US006962776B2

(12) United States Patent
Kopecky et al.

(10) Patent No.: US 6,962,776 B2
(45) Date of Patent: Nov. 8, 2005

(54) METHODS AND MATERIALS FOR EVALUATING CARDIOVASCULAR CONDITIONS

(75) Inventors: Stephen L. Kopecky, Rochester, MN (US); Jorg J. Goronzy, Rochester, MN (US); Cornelia M. Weyand, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 709 days.

(21) Appl. No.: 09/792,686

(22) Filed: Feb. 23, 2001

(65) Prior Publication Data

US 2003/0068645 A1 Apr. 10, 2003

(51) Int. Cl.[7] ............................ G01N 33/53; C12P 21/02
(52) U.S. Cl. ............................ 435/4; 435/7.2; 435/69.1; 435/69.5; 436/501
(58) Field of Search ............................ 435/4, 7.2, 69.1, 435/69.5; 436/501

(56) References Cited

PUBLICATIONS

Adams, "Molecules in Focus—Thrombospondin–1," *Int. J. Biochem. Cell Biol.*, 1997, 29(6):861–865.
Adams et al., "Muskelin, a novel intracellular mediator of cell adhesive and cytoskeletal responses to thrombospondin–1," *EMBO J.*, 1998, 17(17):4964–4974.
Ansel et al., "A chemokine–driven positive feedback loop organizes lymphoid follicles," *Nature*, 2000, 406:309–314.
Arai et al., "Cytokines: Coordinators of Immune and Inflammatory Responses," *Annu. Rev. Biochem.*, 1990, 59:783–836.
Banerjee et al., "Expression of Cdc2 and Cyclin B1 in *Helicobacter pylori*–Associated Gastric MALT and MAST Lymphoma," *Am. J. Pathol.*, 2000, 156:217–225.
Biasucci et al., "Elevated Levels of Interleukin–6 in Unstable Angina," *Circulation*, 1996, 94:874–877.
Blumgart et al., "Studies on the Relation of the Clinical Manifestations of Angina Pectoris, Coronary Thrombosis, and Myocardial Infarction to the Pathological Findings," *Am. Heart J.*, 1940, 19:1–91.
Boehm et al., "Cellular Responses to Interferon–γ," *Annu. Rev. Immunol.*, 1997, 15:749–795.
Bofill et al., "Follicular dendritic cells share a membrane–bound protein with fibroblasts," *J. Pathol.*, 2000, 191:217–226.
Brack et al., "Glucocorticoid–mediated Repression of Cytokine Gene Transcription in Human Arteritis–SCID Chimeras," *J. Clin. Invest.*, 1997, 99(12):2842–2850.
Brichard et al., "The Tyrosinase Gene Codes for an Antigen Recognized by Autologous Cytolytic T Lymphocytes in HLA–A2 Melanomas," *J. Exp. Med.*, 1993, 178:489–495.

Browning et al., "Characterization of Surface Lymphotoxin Forms," *J. Immunol.*, 1995, 154:33–46.
Browning et al., "Signaling through the Lymphotoxin β Receptor Induces the Death of Some Adenocarcinoma Tumor Lines," *J. Exp. Med.*, 1996, 183:867–878.
Braunwald et al., "Unstable Angina: Diagnosis and Management," Clinical Practice Guideline No. 10, AHCPR Publication No. 94–0602, May 1994, Rockville, MD: Agency for Health Care Policy and Research and the National Heart, Lung, and Blood Institute, Public Health Service, U.S. Department of Health and Human Services.
Buja and Willerson, "Role of Inflammation in Coronary Plaque Disruption," *Circulation*, 1994, 89:503–505.
Burleigh et al., "Collagen types I and III, collagen content, GAGs and mechanical strength of human atherosclerotic plaque caps: span–wise variations," *Atherosclerosis*, 1992, 96:71–81.
Cannella et al., "Antibodies to lymphotoxin α (LTα) and LTβ recognize different glial cell types in the central nervous system," *J. Neuroimmunol.*, 1997, 78:172–179.
Chambers and Allison, "Co–stimulation in T cell responses," *Curr. Opin. Immunol.*, 1997, 9:396–404.
Chesebro et al., "Pathogenesis of Thrombosis in Coronary Artery Disease," *Haemostasis*, 1997, 27(Suppl. 1):12–18.
Choi et al., "Interaction of *Staphylococcus aureus* toxin "superantigens" with human T cells," *Proc. Natl. Acad. Sci. USA*, 1989, 86:8941–8945.
Cooper et al., "Transendothelial migration of neutrophils involves integrin–associated protein (CD47)," *Proc. Natl. Acad. Sci. USA*, 1995, 92:3978–3982.
Croft, "Activation of naive, memory and effector T cells," *Curr. Opin. Immunol.*, 1994, 6:431–437.
Cuff et al., "Differential Induction of Adhesion Molecule and Chemokine Expression by LTα3 and LTαβ in Inflammation Elucidates Potential Mechanisms of Mesenteric and Peripheral Lymph Node Development," *J. Immunol.*, 1999, 162:5965–5972.
Cyster, "Chemokines and Cell Migration in Secondary Lymphoid Organs," *Science*, 1999, 286:2098–2102.

(Continued)

*Primary Examiner*—Gary Kunz
*Assistant Examiner*—Fozia Hamud
(74) *Attorney, Agent, or Firm*—Fish & Richardson P.C., P.A.

(57) ABSTRACT

The invention provides methods and materials for evaluating cardiovascular conditions (e.g., angina conditions). Specifically, the invention provides methods and materials related to determining whether or not a mammal has at least one unstable plaque. The invention also provides kits for assessing cardiovascular conditions, substantially pure populations of cells, and methods of identifying compounds to treat life-threatening cardiovascular conditions (e.g., unstable angina).

12 Claims, 12 Drawing Sheets

OTHER PUBLICATIONS

Cyster et al., "Chemokines and B–cell Homing to Follicles," *Current Topics in Microbiology and Immunology*, 1999, 246:87–92.

Cyster, "Leukocyte migration: Scent of the T zone," *Curr. Biol.*, 2000, 10:R30–R33.

Danesh et al., "Chronic infections and coronary heart disease: is there a link?" *Lancet*, 1997, 350:430–436.

Darnell, "STATs and Gene Regulation," *Science*, 1997, 277:1630–1635.

Davies and Thomas, "Plaque fissuring—the cause of acute myocardial infarction , sudden ischaemic death, and crescendo angina," *Br. Heart J.*, 1985, 53:363–373.

Davies et al., "Intramyocardial platelet aggregation in patients with unstable angina suffering sudden ischemic cardiac death," *Circulation*, 1986, 73(3):418–427.

Davies et al., "Risk of thrombosis in human atherosclerotic plaques: role of extracellular lipid, macrophage, and smoth muscle cell content," *Br. Heart J.*, 1993, 69:377–381.

Daviet and McGregor, "Vascular Biology of CD36: Roles of this New Adhesion Molecule Family in Different Disease States," *Thromb. Haemost.*, 1997, 78:65–69.

de Feyter et al., "Ischemia–Related Lesion Characteristics in Patients with Stable or Unstable Angina," *Circulation*, 1995, 92:1408–1413.

de Servi et al., "Expression of Neutrophil and Monocyte CD11B/CD18 Adhesion Molecules at Different Sites of the Coronary Tree in Unstable Angina Pectoris," *Am. J. Cardiol.*, 1996, 78:564–568.

De Togni et al., "Abnormal Development of Peripheral Lymphoid Organs in Mice Deficient in Lymphotoxin," *Science*, 1994, 264:703–707.

DeWood et al., "Prevalance of Total Coronary Occlusion During the Early Hours of Transmural Myocardial Infarction," *N. Engl. J. Med.*, 1980, 303(16):897–902.

Dobson et al., "Changes in estimated coronary risk in the 1980s: data from 38 populations in the Who Monica Project," *Ann. Med.*, 1998, 30:199–205.

Falciani et al., "Elevated Tissue Factor and Tissue Factor Pathway Inhibitor Circulating Levels in Ischaemic Heart Disease Patients," *Thromb. Haemost.*, 1998, 79:498–499.

Falk et al., "Coronary Plaque Disruption," *Circulation*, 1995, 92:657–671.

Farkouh et al., "A Clinical Trial of a Chest–Pain Observation Unit for Patients with Unstable Angina," *N. Eng. J. Med.*, 1998, 339:1882–1888.

Fehr et al., "Correlation of anti–viral B cell responses and splenic morphology with expression of B cell–specific molecules," *Int. Immunol.*, 2000, 12(9):1275–1284.

Förster et al., "Expression of the G–Protein–Coupled Receptor BLR1 Defines Mature, Recirculating B Cells and a Subset of T–Helper Memory Cells," *Blood*, 1994, 84(3):830–840.

Förster et al., "A Putative Chemokine Receptor, BLR1, Directs B Cell Migration to Defined Lymphoid Organs and Specific Anatomic Compartments of the Spleen," *Cell*, 1996, 87:1037–1047.

Förster et al., "CCR7 Coordinates the Primary Immune Response by Establishing Functional Microenvironments in Secondary Lymphoid Organis," *Cell*, 1999, 99:23–33.

Freni et al., "Focal Lymphocytic Aggregates in Chronic Hepatitis C: Occurrence, Immunohistochemical Characterization, and Relation to Markers of Autoimmunity," *Hepatology*, 1995, 22:389–394.

Frieda et al., "Recombinant GST/CD36 Fusion Proteins Define a Thrombospondin Binding Domain," *J. Biol. Chem.*, 1995, 270(7):2981–2986.

Fu et al., "Lymphotoxin–α (LTα) Supports Development of Splinic Follicular Structure That Is Required for IgG responses," *J. Exp. Med.*, 1997, 185:2111–2120.

Fuster et al., "The Pathogenesis of Coronary Artery Disease and the Acute Coronary Syndromes," *N. Engl. J. Med.*, 1992, 326(5):310–318.

Fuster, "Lewis A. Conner Memorial Lecture—Mechanisms Leading to Myocardial Infarction: Insights From Studies of Vascular Biology," *Circulation*, 1994, 90(4):2126–2146.

Fütterer et al., "The Lymphotoxin β Receptor Controls Organogenesis and Affinity Maturation in Peripheral Lymphoid Tissues," *Immunity*, 1998, 9:59–70.

Fyfe et al., "Association Between Serum Amyloid A Proteins and Coronary Artery Disease," *Circulation*, 1997, 96:2914–2919.

Galis et al., "Increased Expression of Matrix Metalloproteinases and Matrix Degrading Activity in Vulnerable Regions of Human Atherosclerotic Plaques," *J. Clin. Invest.*, 1994, 94:2493–2503.

Gao et al., "Integrin–associated Protein Is a Receptor for the C–terminal Domain of Thrombospondin," *J. Biol. Chem.*, 1996, 271:21–24.

Geng et al., "Expression of the Macrophage Scavenger Receptor in Atheroma," *Arterioscler. Thromb. Vasc. Biol.*, 1995, 15:1995–2002.

Germain, "MHC–Dependent Antigen Processing and Peptide Presentation: Providing Ligands for T Lymphocyte Activation," *Cell*, 1994, 76:287–299.

Goronzy et al., "Dominant Clonotypes in the Repertoire of Peripheral CD4+ T Cells in Rheumatoid Arthritis," *J. Clin. Invest.*, 1994, 94:2068–2076.

Grewal and Flavell, "The Role of CD40 Ligand in Costimulation and T–Cell Activation," *Immunol. Rev.*, 1996, 153:85–106.

Grewal et al., "The CD40–CD154 system in anti–infective host defense," *Curr. Opin. Immunol.*, 1997, 9:491–497.

Grewal and Flavell, "The CD40 Ligand," *Immunol. Res.*, 1997, 16:59–70.

Gunn et al., "Mice Lacking Expression of Secondary Lymphoid Organ Chemokine Have Defects in Lymphocyte Homing and Dendritic Cell Localization," *J. Exp. Med.*, 1999, 189(3):451–460.

Gupta et al., "Elevated *Chlamydia pneumoniae* Antibodies, Carciovascular Events, and Azithromycin in Male Survivors of Myocardial Infarction," *Circulation*, 1997, 96:404–407.

Gupta et al., "IFN–γ Potentiates Atherosclerosis in ApoE Knock–out Mice," *J. Clin. Invest.*, 1997, 99(11):2752–2761.

Gupta, "Chlamydia pneumoniae, monocyte activation, and azithromycin in coronary heart disease," *Am. Heart J.*, 1999, 138:S539–S541.

Gurfinkel et al., "Randomised trial of roxithromycin in non–Q–wave coronry syndromes: ROXIS pilot study," *Lancet*, 1997, 350:404–407.

Hansson et al., "Detection of Activated T Lymphocytes in the Human Atherosclerotic Plaque," *Am. J. Pathol.*, 1989, 135:169–175.

Hansson, "Cell–mediated immunity in atherosclerosis," *Curr. Opin. Lipidol.*, 1997, 8:301–311.

Hathcock and Hodes, "Role of the CD28–B7 Costimulatory Pathways in T Cell–Dependent B Cell Responses," *Adv. Immunol.*, 1996, 62:131–166.

Haverkate et al., "Production of C-reactive protein and risk of coronary events in stable and unstable angina," *Lancet*, 1997, 349:462–466.

Hjelmström et al., "Lymphoid Tissue Homing Chemokines Are Expressed in Chronic Inflammation," *Am. J. Pathol.*, 2000, 156(4):1133–1138.

Hsieh et al., "A Simple Method of Sample Size Calculation for Linear and Logistic Regression," *Statist. Med.*, 1998, 17:1623–1634.

Huh et al., "Regulated Expression of CD36 During Monocyte-to-Macrophage Differentiation: Potential Role of CD36 in Foam Cell Formation," *Blood*, 1996, 87(5):2020–2028.

Imai and Yamakawa, "Morphology, function and pathology of follicular dendritic cells," *Pathol. Int.*, 1996, 46:807–833.

Jander et al., "Inflammation in High-Grade Carotid Stenosis—A Possible Role for Macrophages and T Cells in Plaque Destabilization," *Stroke*, 1998, 29:1652–1630.

Jude et al., "Evidence for Time-Dependent Activation of Monocytes in the Systemic Circulation in Unstable Angina But Not in Acute Myocardial Infarction or in Stable Angina," *Circulation*, 1994, 90:1662–1668.

Kaartinen et al., "Accumulation of Activated Mast Cells in the Shoulder Region of Human Coronary Atheroma, the Predilection Site of Atheromatous Rupture," *Circulation*, 1994, 90:1669–1678.

Klatt et al., *Robbins Review of Pathology*, 2000, W. B. Saunders Company, Philadelphia (Table of Contents only).

Kielian and Blecha, "CD14 and other recognition molecules for lipopolysaccharide: a review," *Immunopharmacology*, 1995, 29:187–205.

Klimiuk et al., "Tissue Cytokine Patterns Distinguish Variants of Rheumatoid Synovitis," *Am. J. Pathol.*, 1997, 151(5):1311–1319.

Koni et al., "Distinct Roles in Lymphoid Organogenesis for Lymphotoxins α and β Revealed in Lymphotoxin β–Deficient Mice," *Immunity*, 1997, 6:491–500.

Kovanen et al., "Infiltrates of Activated Mast Cells at the Site of Coronary Atheromatous Erosion or Rupture in Myocardial Infarction," *Circulation*, 1995, 92:1084–1088.

Kovarik et al., "Stat1 combines signals derived from IFN-γ and LPS receptors during macrophage activation," *EMBO J.*, 1998, 17(13):3660–3668.

Kragel et al., "Morphometric Analysis of the Composition of Coronary Arterial Plaques in Isolated Unstable Angina Pectoris with Pain at Rest," *Am. J. Cardiol.*, 1990, 66:562–567.

Kratz et al., "Chronic Inflammation Caused by Lymphotoxin Is Lymphoid Neogenesis," *J. Exp. Med.*, 1996, 183:1461–1472.

Kristensen et al., "Insights Into the Pathophysiology of Unstable Coronary Artery Disease," *Am. J. Cardiol.*, 1997, 80(5A):5E–9E.

Lennert and Schmid, "Prelymphoma, Early Lymphoma, and Manifest Lymphoma in Immunosialadenitis (Sjögren's Syndroma)—A Model of Lymphomagenesis," *Haematol. Blood Transf.*, 1983, 28:418–422.

Lenschow et al., "CD28/B7 System of T Cell Costimulation," *Annu. Rev. Immunol.*, 1996, 14:233–258.

Leonard and O'Shea, "JAKS and STATS: Biological Implications," *Annu. Rev. Immunol.*, 1998, 16:293–322.

Li et al., "Increased Expression of 72–kd Type IV Collagenase (MMP–2) in Human Aortic Atherosclerotic Lesions," *Am. J. Pathol.*, 1996, 148:121–128.

Libby, "Molecular Bases of the Acute Coronary Syndromes," *Circulation*, 1995, 91:2844–2850.

Libby et al., "Macrophages and atherosclerotic plaque stability," *Curr. Opin. Lipidol.*, 1996, 7:330–335.

Libby et al., "Roles of Infectious Agents in Atherosclerosis and Restenosis—An Assessment of the Evidence and Need for Future Research," *Circulation*, 1997, 96:4095–4103.

Lindberg et al., "RH–related Antigen CD47 Is the Signal–transducer Integrin–associated Protein," *J. Biol. Chem.*, 1994, 269(3):1567–1570.

Lindberg et al,. "Decreased Resistance to Bacterial Infection and Granulocyte Defects in IAP–Deficient Mice," *Science*, 1996, 274:795–798.

Lindhout et al., "Fibroblast-Like Synoviocytes from Rheumatoid Arthritis Patients Have Intrinsic Properties of Follicular Dendritic Cells," *J. Immunol.*, 1999, 162:5949–5956.

Linsley and Ledbetter, "The Role of the CD28 Receptor During T Cell Responses to Antigen," *Annu. Rev. Immunol.*, 1993, 11:191–212.

Liu et al., "Follicular Dendritic Cells Specifically Express the Long CR2/CD21 Isoform," *J. Exp. Med.*, 1997, 185:165–170.

Liuzzo et al., "The Prognostic Value of C–Reactive Protein and Serum Amyloid A Protein In Severe Unstable Angina," *N. Engl. J. Med.*, 1994, 331(7):417–424.

Liuzzo et al., "Perturbation of the T–Cell Repertoire in Patients With Unstable Angina," *Circulation*, 1999, 100:2135–2139.

Lopes–Virella et al., "The uptake of LDL–IC by human macrophages: predominant involvement of the FcγRI receptor," *Atherosclerosis*, 1997, 135:161–170.

Luther et al., "BLC Expression in Pancreatic Islets Causes B Cell Recruitment and Lymphotoxin–Dependent Lymphoid Neogenesis," *Immunity*, 2000, 12:471–481.

Mach et al., "Activation of Monocyte/Macrophage Functions Related to Acute Atheroma Complication by Ligation of CD40," *Circulation*, 1997, 96:396–399.

Mach et al., "Functional CD40 ligand is expressed on human vascular endothelial cells, smooth muscle cells, and macrophages: Implications for CD40–CD40 ligand signaling in atherosclerosis," *Proc. Natl. Acad. Sci. USA*, 1997, 94:1931–1936.

Mach et al., "CD40 signaling in vascular cells: A key role in atherosclerosis?" *Atherosclerosis*, 1998, 137(Suppl.):S89–S95.

Mach et al., "Reduction of atherosclerosis in mice by inhibition of CD40 signalling," *Nature*, 1998, 394:200–203.

Mach et al., "Differential expression of three T lymphocyte–activating CXC chemokines by human atheroma–associated cells," *J. Clin. Invest.*, 1999, 104(8):1041–1050.

Manten et al, "Procoagulant and proinflammatory activity in acute coronary syndromes," *Cardiovasc. Res.*, 1998, 40:389–395.

Martens et al., "Expansion of Unusual CD4+ T Cells in Severe Rheumatoid Arthritis," *Arthritis Rheum.*, 1997, 40(6):1106–1114.

Matsumoto et al., "Affinity maturation without germinal centers in lymphtoxin–α–deficient mice," *Nature*, 1996, 382:462–466.

Matsumoto et al., "Lymphotoxin–α–deficient and TNF receptor–I–deficient mice define developmental and functional characeristics of germinal centers," *Immunol.Rev.*, 1997, 156:137–144.

Matsumoto et al., "Distinct Roles of Lymphotoxin α and the Type I Tumor Necrosis Factor (TNF) Receptor in the Establishment of Follicular Dendritic Cells from Non–Bone Marrow–derived Cells," *J. Exp. Med.*, 1997, 186(12):1997–2004.

Mazzone et al., "Increased Expression of Neutrophil and Monocyte Adhesion Molecules in Unstable Coronary Artery Disease," *Circulation*, 1993, 88:358–363.

McKenzie and Schreiber, "Fcγ receptors in phagocytes," *Curr. Opin. Hematol.*, 1998, 5:16–21.

Mehta et al., "Interactive Role of Infection, Inflammation and Traditional Risk Factors in Atherosclerosis and Coronary Artery Disease," *JACC*, 1998, 31(6):1217–1225.

Moreno et al., "Macrophage Infiltration in Acute Coronary Syndromes," *Circulation*, 1994, 90:775–778.

Moreno et al., "Macrophages, Smooth Muscle Cells, and Tissue Factor in Unstable Angina," *Circulation*, 1996, 94:3090–3097.

Nacy and Meltzer, "T–cell–mediated activation of macrophages," *Curr. Opin. Immunol.*, 1991, 3:330–335.

Nakano et al., "A Novel Mutant Gene Involved in T–Lymphocyte–Specific Homing Into Peripheral Lymphoid Organs on Mouse Chromosome 4," *Blood*, 1998, 91(8):2886–2895.

Namekawa et al., "Functional Subsets of CD4 T Cells in Rheumatoid Synovitis," *Arthritis Rheum.*, 1998, 41(12):2108–2116.

Namekawa et al., "Killer Cell Activating Receptors Function as Costimulatory Molecules on $CD4^+CD28^{null}$ T Cells Clonally Expanded in Rheumatoid Arthritis," *J. Immunol.*, 2000, 165:1138–1145.

Neville et al., "The Immunobiology of Interferon–gamma Inducible Protein 10 kD (IP–10): a Novel, Pleiotropic Member of the C–X–C Chemokine Superfamily," *Cytokine Growth Factor Rev.*, 1997, 8(3):207–219.

Ngo et al., "Lymphotoxin α/β and Tumor Necrosis Factor Are Required for Stromal Cell Expresion of Homing Chemokines in B and T Cell Areas of the Spleen," *J. Exp. Med.*, 1999, 189(2):403–412.

O'Brien et al., "Lipoprotein Lipase Is Synthesized by Macrophage–derived Foam Cells in Human Coronary Atherosclerotic Plaques," *J. Clin. Invest.*, 1992, 89:1544–1550.

Park et al., "Co–stimulatory pathways controlling activation and peripheral tolerance of human $CD4^+28^-$ T cells," *Eur., J. Immunol.*, 1997, 27:1082–1090.

Parkos et al, "CD47 Mediates Post–adhesive Events Required for Neutropil Migration Across Polarized Intestinal Epithelial," *J. Cell Biol.*, 1996, 132(3):437–450.

Pasceri et al., "A Tale of Two Diseases—Atherosclerosis and Rheumatoid Arthritis," *Circulation*, 1999, 100:2124–2126.

Pine, "Convergence of TNFα and IFNγ signaling pathways through syndergistic induction of IRF–I/ISGF–2 is mediated by a composite GAS/κB promoter element," *Nucl. Acids Res.*, 1997, 25(21):4346–4354.

Rajagopalan et al., "Reactive Oxygen Species Produced by Macrophage–derived Foam Cells Regulate the Activity of Vascular Matrix Metalloproteinases In Vitro," *J. Clin. Invest.*, 1996, 98(11):2572–2579.

Rajavashisth et al., "Membrane Type 1 Matrix Metalloproteinase Expression in Human Atherosclerotic Plaques," *Circulation*, 1999, 99:3103–3109.

Reinhold et al., "Costimulation of T Cell Activation by Integrin–associated Protein (CD47) Is an Adhesion–dependent, CD28–independent Signaling Pathway," *J. Exp. Med.*, 1997, 185:1–11.

Ridker, "Novel Risk Factors and Markers for Coronary Disease," *Adv. Internal Med.*, 2000, 45:391–418.

Riessen et al., "Immunolocalization of thrombospondin–1 in human atherosclerotic and restenotic arteries," *Am. Heart J.*, 1998, 135:357–364.

Rincon and Flavell, "T–cell subsets: Transcriptional control in the Th1/Th2 decision," *Curr. Biol.*, 1997, 7:R729–R732.

Robey and Allison, "T–cell activation: integration of signals from the antigen receptor and constimulatory molecules," *Immunol. Today*, 1995, 16(7):306–310.

Ross, "Atherosclerosis is an inflammatory disease," *Am. J. Heart J.*, 1999, 138:S419–S420.

Rudd, "Upstream–Downstream: CD28 Cosignaling Pathways and T Cell Function," *Immunity*, 1996, 4:527–534.

Ruddle, "Lymphoid Neo–organogenesis," *Immunologic Res.*, 1999, 19(2–3):119–125.

Russell, "Activation–induced death of mature T cells in the regulation of immune responses," *Curr. Opin. Immunol.*, 1995, 7:382–388.

Schaper and Buschmann, "Arteriogenesis, the good and the bad of it," *Cardiovasc. Res.*, 1999, 43:835–837.

Schiff et al., "Increased Phagocyte FcγRI Expression and Improved Fcγ–Receptor–Mediated Phagocytosis After In Vivo Recombinant Human Interferon–γ Treatment of Normal Human Subjects," *Blood*, 1997, 90(8):3187–3194.

Schinder and Strehlow, "Cytokines and STAT Signaling," *Hormones and Signaling, Adv. Pharmacol.*, 2000, 47:113–174.

Schirmer et al., "Resistance to Apoptosis and Elevated Expression of Bcl–2 in Clonally Expanded $CD4^+CD28^-$ T Cells from Rheumatoid Arthritis Patients," *J. Immunol.*, 1998, 161:1018–1025.

Schmidt et al., "$CD4^+$ $CD7^-$ $CD28^-$ T Cells Are Expanded in Rheumatoid Arthritis and Are Characterized by Autoreactivity," *J. Clin. Invest.*, 1996, 97:2027–2037.

Schmidt et al., "The Repertoire of $CD4^+$ T Cells in Rheumatoid Arhtritis," *Mol. Med.*, 1996, 2(5):608–618.

Schröder et al., "Differentiation of B cells in the nonlymphoid tissue of the synovial membrane of patients with rheumaotid arthritis," *Proc. Natl. Acad. Sci. USA*, 1996, 93:221–225.

Schumacher et al., "Increased Neopterin in Patients With Chronic and Acute Coronary Syndromes," *JACC*, 1997, 30(3):703–707.

Serneri et al., "Monocyte activation and increased procoagulant activity in unstable angina," *Lancet*, 1990, 336(8728):1444–1445.

Serneri et al., "Transient Intermittent Lympocyte Activation Is Responsible for the Instability of Angina," *Circulation*, 1992, 86:790–797.

Serneri et al., "Acute T–Cell Activation Is Detectable in Unstable Angina," *Circulation*, 1997, 95:1806–1812.

Shah, "Pathophysiology of Plaque Rupture and the Concept of Plaque Stabilization," *Cardiol. Clin.*, 1996, 14:17–29.

Shah, "Plaque Disruption and Coronary Thrombosis: New Insight into Pathogenesis and Prevention," *Clin. Cardiol.*, 1997, 20(Suppl. II):II–38–II–44.

Shah, "Plaque Disruption and Thrombosis," *Cardiol. Clin.*, 1999, 17(2):271–281.

Sherman et al., "Coronary Angioscopy in Patients with Unstable Angina Pectoris," *N. Engl. J. Med.*, 1986, 315(15):913–919.

Small, "George Lyman Duff Memorial Lecture—Progression and Regression of Atherosclereotic Lesions," *Arteriosclerosis*, 1988, 8:103–129.

Stemme et al., "T Lymphocytes in Human Atherosclerotic Plaques Are Memory Cells Expressing CD45RO and the Integrin VLA–1," *Arterioscl. Thromb.*, 1992, 12:206–211.

Taubman et al., "Tissue Factor in the Pathogenesis of Atherosclerosis," *Thromb. Haemost.*, 1997, 78:200–204.

Théroux and Fuster, "Acute Coronary Syndromes—Unstable Angina and Non–Q–Wave Myocardial Infarction," *Circulation*, 1998, 97:1195–1206.

Ticchioni et al., "Integrin–Associated Protein (CD47) Is a Comitogenic Molecule on CD–3–Activated Human T Cells," *J. Immunol.*, 1997, 158:677–684.

Toschi et al., "Tissue Factor Modulates the Thrombogenicity of Human Atherosclerotic Plaques," *Circulation*, 1997, 95:594–599.

Vallejo and Pease, "The Locus–specific Enhancer Activity of the Class I Major Histocompatibility Complex Interferon–responsive Element is Associated with a γ–Interferon (IFN)–inducible Fator Distinct from STAT1α, p48, and IFN Regulatory Factor–1," *J. Biol. Chem.*, 1996, 271(47):29813–29821.

Vallejo et al., "Aging–related Deficiency of CD28 Expression in $CD4^+$ T Cells Is Associated with Loss of Gene–specific Nuclear Factor Binding Activity," *J. Biol. Chem.*, 1998, 273(14):8119–8129.

Valtonen, "Role of infections in atherosclerosis," *Am. Heart J.*, 1999, 138:S431–S433.

van der Wal et al., "Site of Intimal Rupture or Erosion of Thrombosed Coronary Atherosclerotic Plaques Is Characterized by an Inflammatory Process Irrespective of the Dominant Plaque Morphology," *Circulation*, 1994, 89:36–44.

Vassileva et al., "The Reduced Expression of 6Ckine in the plt Mouse Results from the Deletion of One of Two 6Ckine Genes," *J. Exp. Med.*, 1999, 190(8):1183–1188.

Waase et al., "Oligoclonal T Cell Proliferation in Patients with Rheumatoid Arthritis and Their Unaffected Siblings," *Arithritis Rheum.*, 1996, 39(6):904–913.

Waclavicek et al., "T Cell Stimulation via CD47: Agonistic and Antagonistic Effects of CD47 Monoclonal Antibody 1/1A4," *J. Immunol.*, 1997, 159:5345–5354.

Wagner et al., "The SIF binding element confers sis/PDGF inducibility onto the c–fos promoter," *EMBO J.*, 1990, 9(13):4477–4484.

Wagner et al., "Interferon–γ–Producing T Cells in Giant Cell Vasculitis Represent a Minority of Tissue–Infiltrating Cells and Are Located Distant from the Site of Pathology," *Am. J. Pathol.*, 1996, 148(6):1925–1933.

Wagner et al., "The Role of $CD8^+$ $CD40L^+$ T Cells in the Formation of Germinal Centers in Rheumatoid Synovitis," *J. Immunol.*, 1998, 161:6390–6397.

Wang et al., "Interferon–inducible Protein–10 Involves Vascular Smooth Muscle Cell Migration, Proliferation, and Inflammatory Response," *J. Biol. Chem.*, 1996, 271(39):24286–24293.

Weyand et al., "Correlation of the Topographical Arrangement and the Functional Pattern of Tissue–infiltrating Macrophages in Giant Cell Arteritis," *J. Clin. Invest.*, 1996, 98(7):1642–1649.

Weyand et al., "Functional properties of $CD4^+$ $CD28^+$ T cells in the aging immune system," *Mech. Ageing Dev.*, 1998, 102:131–147.

Weyand et al., "Cell–cell interactions in synovitis—Interactions between T cells and B cells in rheumatoid arthritis," *Arthritis Res.*, 2000, 2:457–463.

Wieand et al., "A family of nonparametric statistics for comparing diagnostic markers with paired or unpaired data," *Biometrika*, 1989, 76(3):585–592.

Witztum, "The oxidation hypothesis of atherosclerosis," *Lancet*, 1994, 344:793–795.

Young et al., "Immunohistologic Characterization of Synovial Membrane Lymphocytes in Rheumatoid Arthritis," *Arthritis Rheum.*, 1984, 27:32–39.

Zhou et al., "Evidence for a Local Immune Response in Atherosclerosis," *Am. J. Pathol.*, 1996, 149(2):359–366.

De Servi et al., "Significance of increased plasma levels of imflammatory mediators in unstable angina," *Eur. Heart J.*, 1999, 20 (Abstract Suppl.):399, Abstract #P2117.

Liuzzo et al., "Disease Specific Patterns of Cytokine Production by T–Lymphocytes in Coronary Atheroslcerosis: Evidence for a Role of Infectious Agents in the Pathogenesis of Unstable Angina," *JACC*, 1998, 31(2—Suppl. A):187A, Abstract #839–3.

Liuzzo et al., "T Cell Function in Unstable Angina: Increased Interferon–g Production by Unusual T lymphocytes," *Circulation*, 1998, 98(17—Suppl.):1171, Abstract #882.

Liuzzo et al., "Monocytes from Unstable Angina Patients Express a Molecular Fingerprint of Interferon–Gamma Mediated Activation," *Circulation*, 2000, 102(18—Suppl.):II–777, Abstract # 3753.

Liuzzo et al., "Molecular Fingerprint of Interferon–γ Signaling in Unstable Angina," *Circulation*, 2001, 103(11):1509–1514.

METHODS AND MATERIALS FOR EVALUATING CARDIOVASCULAR CONDITIONS

BACKGROUND

1. Technical Field

The invention relates to methods and materials involved in evaluating cardiovascular conditions. Specifically, the invention relates to methods and materials involved in determining whether or not a mammal has an unstable plaque.

2. Background Information

Coronary artery disease is characterized by long periods of clinical stability with few or no symptoms. In addition, classical pathologic studies have demonstrated that the disease is commonly far advanced anatomically before any symptoms are reported (Blumgart H L et al., *Am. Heart Journal*, 19:1 (1940)). An additional characteristic of coronary artery disease is a propensity to an abrupt, sometimes catastrophic, change in a previous stable or silent clinical course leading to a variety of acute coronary syndromes (Fuster V et al., *N. Engl. J. Med.* 326:310–318 (1992)).

SUMMARY

The invention involves evaluating cardiovascular conditions. Specifically, the invention provides methods and materials related to determining whether or not a mammal has an unstable plaque. In addition, the invention provides methods and materials related to determining whether or not a mammal is at risk for developing an unstable plaque. The invention also provides kits for assessing cardiovascular conditions, substantially pure populations of cells, and methods of identifying compounds that can be used to treat a life-threatening cardiovascular condition (e.g., unstable angina) or reduce the risk of developing a life-threatening cardiovascular condition (e.g., the presence of unstable plaques).

The term "cardiovascular condition" as used herein refers to symptomatic (e.g., angina conditions) and asymptomatic coronary artery disease. The term "angina condition" as used herein refers to a cardiovascular condition where the mammal experiences chest pain resulting from an inadequate delivery of oxygen to the heart muscle. Typically, this chest pain is characterized as a heavy or squeezing pain in the midsternal area of the chest. Angina conditions can be either stable or unstable. In general, stable angina refers to an angina condition that is not changing in severity, duration, or frequency, while unstable angina refers to an angina condition that is increasing in severity, duration, or frequency. Typically, unstable angina patients are at an increased risk of having a myocardial infarction as compared to stable angina patients.

The term "unstable plaque" as used herein refers to an inflamed plaque that can rupture at any time possibly leading to a thrombotic event and/or myocardial infarction. Typically, inflamed plaques are small plaques. The term "stable plaque" as used herein refers to a plaque that is not inflamed. Plaques that are not inflamed typically do not rupture.

The methods and materials described herein can be used to identify mammals having at least one unstable plaque or mammals having an increased risk of developing at least one unstable plaque. Thus, the invention provides methods and materials that can be used to inform medical professionals about the risk a patient faces with respect to experiencing a myocardial infarction. In other words, the methods and materials described herein can be used to screen patients (e.g., patients with angina, patients that smoke, and patients that are overweight) such that those patients with at least one unstable plaque and, therefore, at an increased risk for myocardial infarction are identified and appropriately treated. For example, patients presenting an angina condition can be screened using the methods and materials described herein to identify those patients having unstable plaques. When it is determined that a patient has an unstable plaque, then that patient can be further evaluated by, for example, angiography. Since angiography is typically used to evaluate patients suspected to have unstable angina, the methods and materials provided herein can allow medical professionals reliably determine which patients need further evaluation and which patients do not. In addition, methods and materials described herein can provide important information about a patient's cardiovascular condition (e.g., angina condition) in both an efficient and objective manner.

In general, the invention features a method for determining whether or not a mammal (e.g., human) has an unstable plaque. The method includes determining whether or not a sample from the mammal contains an elevated level of an interferon-γ-activated transcription factor, where the elevated level indicates that the mammal contains the unstable plaque. The sample can be a blood sample and can contain mononuclear cells. The sample can be a nuclear extract. The interferon-γ-activated transcription factor can be a phosphorylated transcriptional factor. The interferon-γ-activated transcription factor can be phosphorylated STAT-1.

In another embodiment, the invention features a method of assisting a person in determining whether or not a mammal has an unstable plaque. The method includes (a) determining the level of an interferon-γ-activated transcription factor in a sample from the mammal, and (b) communicating information about the level to the person, where an elevated level of the interferon-γ-activated transcription factor in the sample indicates that the mammal contains the unstable plaque. The person can be a medical professional (e.g., a doctor, a nurse practitioner, a scientist, and a technician). The communication can include sending the information directly to the person. The communication can include sending the information indirectly to the person. The communication can include making the information electronically available to the person. The interferon-γ-activated transcription factor can be STAT-1.

Another embodiment of the invention features a method for determining whether or not a mammal has an unstable plaque. The method includes determining whether or not a sample from the mammal contains an elevated level of a polypeptide, where the polypeptide is encoded by DNA responsive to an interferon-γ-activated transcription factor, and where the level indicates that the mammal contains the unstable plaque. The sample can contain mononuclear cells. The polypeptide can be CD64 or IP-10. The interferon-γ-activated transcription factor can be STAT-1.

Another embodiment of the invention features a method of assisting a person in determining whether or not a mammal has an unstable plaque. The method includes (a) determining the level of a polypeptide in a sample from the mammal, where the polypeptide is encoded by DNA responsive to an interferon-γ-activated transcription factor, and (b) communicating information about the level to the person, where an elevated level of the polypeptide in the sample indicates that the mammal contains the unstable plaque. The polypeptide can be CD64 or IP-10. The interferon-γ-activated transcription factor can be STAT-1.

Another embodiment of the invention features a method for determining whether or not a mammal has an unstable plaque. The method includes determining whether or not a sample from the mammal contains an elevated level of an mRNA, where the mRNA is encoded by DNA responsive to an interferon-γ-activated transcription factor, and where the elevated level indicates that the mammal contains the unstable plaque. The sample can contain mononuclear cells. The mRNA can be CD64 mRNA or IP-10 mRNA. The interferon-γ-activated transcription factor can be STAT-1.

Another embodiment of the invention features a method of assisting a person in determining whether or not a mammal has an unstable plaque. The method includes (a) determining the level of an mRNA in a sample from the mammal, where the mRNA is encoded by DNA responsive to an interferon-γ-activated transcription factor, and (b) communicating information about the level to the person, where an elevated level of the mRNA in the sample indicates that the mammal contains the unstable plaque. The mRNA can be CD64 mRNA or IP-10 mRNA. The interferon-γ-activated transcription factor can be STAT-1.

In another aspect, the invention features a kit containing at least two different antibodies, where each of the at least two different antibodies specifically recognizes a different polypeptide, and where each different polypeptide is encoded by DNA responsive to an interferon-γ-activated transcription factor. At least one of the at least two different antibodies can be an anti-CD64, anti-IP10, or anti-phosphorylated STAT-1 antibody. At least one of the at least two different antibodies can be labeled. The kit can include a reference chart indicating a reference level for at least one of the polypeptides. The kit can contain an anti-CD161 antibody.

In another embodiment, the invention features a kit containing at least two sets of oligonucleotide primers, where each set amplifies a different target sequence during an amplification reaction, where each different target sequence encodes a different polypeptide, each different polypeptide being a polypeptide that is encoded by DNA responsive to an interferon-γ-activated transcription factor. At least one of the different polypeptides can be CD64, IP-10, or STAT-1. The kit can include a reference chart indicating a reference level for an IFN-γ-responsive mRNA, where at least one of the different target sequences contains a sequence from the IFN-γ-responsive mRNA. The kit can contain a reference chart indicating a reference level for an IFN-γ-responsive polypeptide, where at least one of the different target sequences encodes the IFN-γ-responsive polypeptide. The kit can contain a pair of oligonucleotide primers that amplify, during the amplification reaction, a sequence that encodes CD161 mRNA.

Another aspect of the invention features a substantially pure population of $CD28^{null}$ T cells, where each $CD28^{null}$ T cell contains a T-cell receptor that is present on a $CD28^{null}$ T cell expanded in an unstable angina patient. The $CD28^{null}$ T cells can be isolated from a patient having an unstable angina condition. The $CD28^{null}$ T cells can be $CD4^+$/$CD28^{null}$ T cells or $CD8^+$/$CD28^{null}$ T cells. The $CD28^{null}$ T cells can express interferon-γ or CD161.

In another embodiment, the invention features a substantially pure population of $CD28^{null}$ T cells, where the $CD28^{null}$ T cells recognize an unstable angina antigen.

Another aspect of the invention features a method for determining whether or not an antigenic polypeptide is an unstable angina antigen The method includes (a) contacting an antigen presenting cell presenting the antigenic polypeptide with a $CD28^{null}$ T cell, where the $CD28^{null}$ T cell is expanded in an unstable angina patient, and (b) determining whether or not the $CD28^{null}$ T cell is activated after the contacting, where activation of the $CD28^{null}$ T cell indicates that the antigenic polypeptide is the unstable angina antigen.

Another embodiment of the invention features a method for assessing a compound for inhibitory activity. The method includes (a) contacting an activated $CD28^{null}$ T cell with the compound, and (b) determining whether or not the activation of the activated $CD28^{null}$ T cell is reduced or eliminated after the contacting, where the reduction or elimination of the activation indicates that the compound is an inhibitor of $CD28^{null}$ T cell activation.

Another embodiment of the invention features a method for determining whether or not a mammal has an unstable plaque. The method includes determining whether or not a $CD28^{null}$ T cell from the mammal expresses CD161, where the expression of the CD161 by the $CD28^{null}$ T cell indicates that the mammal contains the unstable plaque.

Another embodiment of the invention features a method of assisting a person in determining whether or not a mammal has an unstable plaque. The method includes (a) determining whether or not a $CD28^{null}$ T cell from the mammal expresses CD161, and (b) communicating information about the expression to the person, where the expression of the CD161 by the $CD28^{null}$ T cell indicates that the mammal contains the unstable plaque.

Another embodiment of the invention features a method for determining whether or not a mammal is at risk for developing an unstable plaque. The method includes determining whether or not a sample from the mammal contains an elevated level of an interferon-γ-activated transcription factor, where the elevated level indicates that the mammal is at risk for developing the unstable plaque.

Another embodiment of the invention features a method of assisting a person in determining whether or not a mammal is at risk for developing an unstable plaque. The method includes (a) determining the level of an interferon-γ-activated transcription factor in a sample from the mammal, and (b) communicating information about the level to the person, where an elevated level of the interferon-γ-activated transcription factor in the sample indicates that the mammal is at risk for developing the unstable plaque.

Another embodiment of the invention features a method for determining whether or not a mammal is at risk for developing an unstable plaque. The method includes determining whether or not a sample from the mammal contains an elevated level of a polypeptide, where the polypeptide is encoded by DNA responsive to an interferon-γ-activated transcription factor, and where the level indicates that the mammal is at risk for developing the unstable plaque.

Another embodiment of the invention features a method of assisting a person in determining whether or not a mammal is at risk for developing an unstable plaque. The method includes (a) determining the level of a polypeptide in a sample from the mammal, where the polypeptide is encoded by DNA responsive to an interferon-γ-activated transcription factor, and (b) communicating information about the level to the person, where an elevated level of the polypeptide in the sample indicates that the mammal is at risk for developing the unstable plaque.

Another embodiment of the invention features a method for determining whether or not a mammal is at risk for developing an unstable plaque. The method includes determining whether or not a sample from the mammal contains an elevated level of an mRNA, where the mRNA is encoded by DNA responsive to an interferon-γ-activated transcription factor, and where the elevated level indicates that the mammal is at risk for developing the unstable plaque.

Another embodiment of the invention features a method of assisting a person in determining whether or not a mammal is at risk for developing an unstable plaque. The method includes (a) determining the level of an mRNA in a sample from the mammal, where the mRNA is encoded by DNA responsive to an interferon-γ-activated transcription factor, and (b) communicating information about the level to the person, where an elevated level of the mRNA in the sample indicates that the mammal is at risk for developing the unstable plaque.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
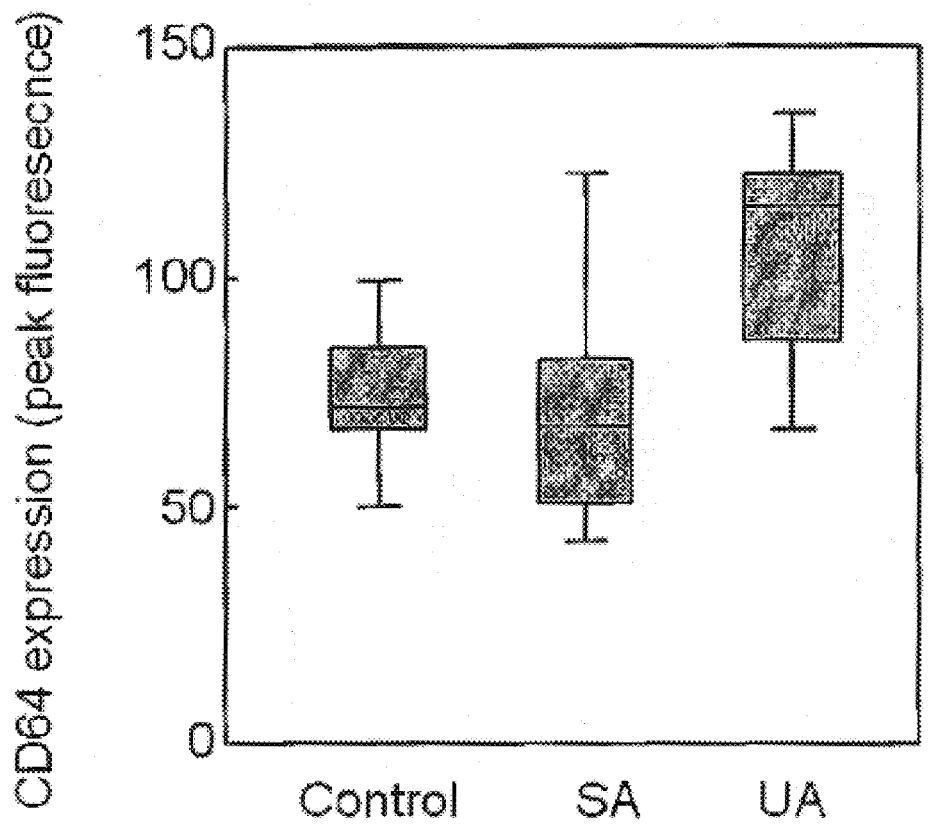
FIG. 1 is a bar graph plotting CD64 expression levels of samples from healthy controls, SA patients, and UA patients. The median value is represented as a line, the 25th and 75th percentiles are represented as boxes, and the 10th and 90th percentiles are represented as whiskers.

The invention provides methods and materials related to evaluating cardiovascular conditions. Specifically, the invention provides methods and materials related to determining the severity of a cardiovascular condition in a mammal (e.g., human, dog, cat, horse, cow, goat, and pig). For example, the invention provides methods and materials for determining whether or not a sample from a mammal contains an elevated level of an interferon-γ-activated transcription factor, an elevated level of a polypeptide encoded by DNA responsive to an interferon-γ-activated transcription factor, and/or an elevated level of mRNA encoded by DNA responsive to an interferon-γ-activated transcription factor. The presence of one or more of these elevated levels can indicate that the mammal contains at least one unstable plaque. The invention also provides kits for assessing the severity of a cardiovascular condition, substantially pure populations of cells, and methods of identifying compounds to treat cardiovascular conditions such as unstable angina.

1. Interferon-γ-activated Transcription Factors

The level of an IFN-γ-activated transcription factor present within a sample obtained from a mammal can be evaluated (1) to determine whether or not the mammal contains at least one unstable plaque or (2) to determine whether or not the mammal has an increased risk for developing an unstable plaque. As disclosed herein, if the level of an IFN-γ-activated transcription factor in a sample is an elevated level, then the mammal can be classified either as having at least one unstable plaque or as having an increased risk of developing an unstable plaque. In the case of a mammal having an angina condition, the angina condition can be classified as unstable. If the level of an TFN-γ-activated transcription factor in a sample is not an elevated level, then the mammal can be classified either as not having at least one unstable plaque or as not having an increased risk of developing an unstable plaque. In the case of a mammal having an angina condition, the angina condition can be classified as stable.

The term "elevated level" as used herein with respect to the level of an IFN-γ-activated transcription factor is any level that is greater than a reference level for that IFN-γ-activated transcription factor. The term "reference level" as used herein with respect to an IFN-γ-activated transcription factor is the level typically expressed by healthy mammals or mammals with SA. For example, a reference level can be the average level of an IFN-γ-activated transcription factor that is present in samples obtained from a random sampling of 50 SA patients.

It will be appreciated that levels from comparable samples are used when determining whether or not a particular level is an elevated level. For example, the average level of a particular IFN-γ-activated transcription factor present in brain tissue from a population of SA patients may be 30 units/g of tissue, while the average level of the same IFN-γ-activated transcription factor present in liver tissue from the same population of SA patients may be 10 units/g of tissue. In this case, the reference level for that particular IFN-γ-activated transcription factor in brain tissue would be 30 units/g of tissue, and the reference level for that particular IFN-γ-activated transcription factor in liver tissue would be 10 units/g of tissue. Thus, when determining whether or not a level of that IFN-γ-activated transcription factor measured in liver tissue is elevated, the measured level would be compared to the reference level for that particular IFN-γ-activated transcription factor in liver tissue (i.e., 10 units/g of tissue).

An elevated level of an IFN-γ-activated transcription factor can be about 0.1, 0.5, 1, 2, 3, 4, 5, 6, 7, 8, 9, 10, 15, 20, or more times greater than a reference level for that IFN-γ-activated transcription factor. In addition, a reference level can be any amount. For example, a reference level for an IFN-γ-activated transcription factor can be zero. In this case, any level of that IFN-γ-activated transcription factor greater than zero would be an elevated level.

The term "IFN-γ-activated transcription factor" as used herein refers to any transcription factor that induces transcription in response to IFN-γ. In addition, an IFN-γ-activated transcription factor is a polypeptide that is present within a cell at the time of IFN-γ stimulation. For example, a transcription factor is considered an IFN-γ-activated transcription factor if that transcription factor (1) is present within a cell and (2) becomes activated upon IFN-γ stimulation such that that transcription factor induces transcription in that cell. A transcription factor is not considered an IFN-γ-activated transcription factor if that transcription factor must first, after IFN-γ stimulation, be synthesized. Examples of IFN-γ-activated transcription factors include, without limitation, STAT-1 and NF-κB.

Any method can be used to identify an IFN-γ-activated transcription factor. For example, a radioactive oligonucleotide having a sequence that is required for an IFN-γ-responsive polypeptide to be expressed in response to IFN-γ can be incubated with a nuclear lysate obtained from cells exposed to IFN-γ. One example of a sequence for such an oligonucleotide is 5'-CGCCATTTCCCGTAAATC-3' (SEQ ID NO: 1). If an IFN-γ-activated transcription factor is present in the nuclear lysate, then an oligonucleotide/IFN-γ-activated transcription factor complex can be formed. The presence of the oligonucleotide/IFN-γ-activated transcription factor complex can be determined by gel electrophoresis since the complex will migrate slower than the oligonucleotide alone. Once detected, the oligonucleotide/IFN-γ-activated transcription factor complex can be isolated, and the identity of the IFN-γ-activated transcription factor determined. In addition, any method can be used to confirm that an IFN-γ-activated transcription factor is present within a cell prior to IFN-γ stimulation. For example, pulse-case experiments or experiments inhibiting transcription and/or translation can be performed to confirm that the transcription factor inducing transcription is present prior to IFN-γ treatment.

In some cases, an IFN-γ-activated transcription factor can be a modified polypeptide such as a phosphorylated polypeptide. Upon modification, the polypeptide can be translocated to the nucleus where it induces transcription. For example, cytoplasmic STAT-1 typically becomes an IFN-γ-activated transcription factor after being phosphorylated in response to the cell being stimulated by IFN-γ. Once phosphorylated, STAT-1 can translocate to the nucleus and induce transcription.

An IFN-γ-activated transcription factor can induce the transcription of any mRNA. For example, an IFN-γ-activated transcription factor can induce the transcription of mRNA that encodes a receptor, an enzyme, a transporter, or an IFN-γ-activated transcription factor. In addition, an IFN-γ-activated transcription factor can induce the transcription of any number of different mRNA molecules. For example, an IFN-γ-activated transcription factor can induce the transcription of one, two, three, four, or more different mRNA molecules.

Any type of sample can be used to evaluate the level of an IFN-γ-activated transcription factor including, without limitation, tissue, blood, and isolated blood cells (e.g., PBMC). In addition, any method can be used to obtain a sample. For example, a syringe can be used to obtain peripheral blood from a mammal. Once obtained, a sample can be manipulated prior to measuring the level of an IFN-γ-responsive transcription factor. For example, a peripheral blood sample can be centrifugated to obtain an enriched cell sample. In addition, a cell sample can be treated such that a nuclear extract is obtained. Once obtained, the nuclear extract can be evaluated to determine the amount of an IFN-γ-activated transcription factor present.

Any method can be used to determine the level of an IFN-γ-activated transcription factor present within a sample. For example, the level of an TFN-γ-activated transcription factor present within a sample can be determined using polypeptide detection methods such as western blot, immunochemistry, and gel shift assays. Typically, the level of phosphorylated STAT-1 can be determined using an antibody specific for phosphorylated STAT-1. Alternatively, the level of phosphorylated STAT-1 can be determined using a nuclear extract and an antibody that does not distinguish between unphosphorylated and phosphorylated STAT-1. In this case, the detection of STAT-1 in a nuclear extract will correlate to phosphorylated STAT-1 since phosphorylated STAT-1 translocates to the nucleus and unphosphorylate STAT-1 does not. The level of phosphorylated STAT-1 also can be determined using a gel shift assay. For example, a nuclear extract can be mixed with a radioactive oligonucleotide containing a sequence recognized by phosphorylated STAT-1 (e.g., 5'-CGCCATTTCCCGTAAATC-3'; SEQ ID NO:1). After mixing, the mixture can be separated by gel electrophoresis to determine the amount of STAT-1 bound to the radioactive oligonucleotide. The STAT-1/oligonucleotide complex will have a slower mobility than the oligonucleotide alone.

2. IFN-γ-responsive mRNA and Polypeptides

The level of an IFN-γ-responsive mRNA or polypeptide in a sample obtained from a mammal can be evaluated (1) to determine whether or not the mammal contains at least one unstable plaque or (2) to determine whether or not the mammal has an increased risk for developing an unstable plaque. The term "IFN-γ-responsive mRNA" as used herein refers to mRNA that is encoded by DNA responsive to an IFN-γ-activated transcription factor. The term "IFN-γ-responsive polypeptide" as used herein refers to a polypeptide that is encoded by DNA responsive to an IFN-γ-activated transcription factor. DNA responsive to an IFN-γ-activated transcription factor is any DNA sequence that is transcribed in a cell to a greater extent in the presence of an IFN-γ-activated transcription factor. Typically, such DNA is located downstream of a regulatory sequence recognized by an IFN-γ-activated transcription factor such that the IFN-γ-activated transcription factor binds to the regulatory sequence and directs transcription of that downstream DNA.

The DNA that encodes an IFN-γ-responsive mRNA or polypeptide can be responsive to any IFN-γ-activated transcription factor including, without limitation, STAT-1 and NF-κB. For example, an IFN-γ-responsive mRNA or polypeptide can be encoded by DNA responsive to STAT-1. Examples of IFN-γ-responsive mRNA include, without limitation, IP-10 mRNA, CD64 mRNA, IFN-γ regulatory factor-1 (IRF1) mRNA, and IFN-γ regulatory factor-2 (IRF2) mRNA. Examples of IFN-γ-responsive polypeptides include, without limitation, IP-10, CD64, IRF1, and IRF2.

Any method can be used to identify an IFN-γ-responsive mRNA or polypeptide. For example, a computer algorithm can be used to search a nucleic acid database (e.g., GenBank®) for a polypeptide-encoding sequence located near a regulatory sequence recognized by an IFN-γ-activated transcription factor. In addition, an IFN-γ-responsive mRNA or polypeptide can be identified by comparing the expression level of an mRNA or polypeptide in a cell treated with IFN-γ (e.g., 50, 100, 200, 250, 500, 1000, 2000, or more Units/mL of IFN-γ) to the expression level of that mRNA or polypeptide in a cell not treated with IFN-γ. Once identified as having increased expression after IFN-γ treatment, the mRNA or polypeptide can be purified and sequenced.

As disclosed herein, if the level of an IFN-γ-responsive mRNA or polypeptide in a sample is an elevated level, then the mammal can be classified either as having at least one unstable plaque or as having an increased risk of developing an unstable plaque. In the case of a mammal having an angina condition, the angina condition can be classified as unstable. If the level of an IFN-γ-responsive mRNA or polypeptide in a sample is not an elevated level, then the mammal can be classified either as not having at least one unstable plaque or as not having an increased risk of developing an unstable plaque. In the case of a mammal having an angina condition, the angina condition can be classified as stable. The term "elevated level" as used herein with respect to the level of an IFN-γ-responsive mRNA or polypeptide is any level that is greater than a reference level for that IFN-γ-responsive mRNA or polypeptide. The term "reference level" as used herein with respect to an IFN-γ-responsive mRNA or polypeptide is the level typically expressed by healthy mammals or mammals with SA. For example, a reference level can be the average level of an IFN-γ-responsive mRNA or polypeptide that is present in samples obtained from a random sampling of 50 SA patients. As described herein, IP-10 mRNA was undetected in blood cells obtained from a population of SA patients. Thus, in this case, any level of IP-10 mRNA or polypeptide detected in blood cells using a similar method can be an elevated level.

It will be appreciated that levels from comparable samples are used when determining whether or not a particular level is an elevated level. For example, the average level of a particular IFN-γ-responsive mRNA or polypeptide present in brain tissue from a population of SA patients may be 30 units/g of tissue, while the average level of the same IFN-γ-responsive mRNA or polypeptide present in liver tissue from the same population of SA patients may be 10 units/g of tissue. In this case, the reference level for that particular IFN-γ-responsive mRNA or polypeptide in brain tissue would be 30 units/g of tissue, and the reference level for that particular IFN-γ-responsive mRNA or polypeptide in liver tissue would be 10 units/g of tissue. Thus, when determining whether or not a level of that IFN-γ-responsive mRNA or polypeptide measured in liver tissue is elevated, the measured level would be compared to the reference level for that particular IFN-γ-responsive mRNA or polypeptide in liver tissue (i.e., 10 units/g of tissue).

An elevated level of an IFN-γ-responsive mRNA or polypeptide can be about 0.1, 0.5, 1, 2, 3, 4, 5, 6, 7, 8, 9, 10, 15, 20, or more times greater than a reference level for that IFN-γ-responsive mRNA or polypeptide. In addition, a reference level can be any amount. For example, a reference level for an IFN-γ-responsive mRNA or polypeptide can be zero. In this case, any level of that IFN-γ-responsive mRNA or polypeptide greater than zero would be an elevated level.

Any type of sample can be used to evaluate the level of an IFN-γ-responsive mRNA or polypeptide including, without limitation, tissue, blood, and isolated blood cells (e.g., PBMC). In addition, any method can be used to obtain a sample. For example, a syringe can be used to obtain peripheral blood from a mammal. Once obtained, a sample can be manipulated prior to measuring the level of an IFN-γ-responsive mRNA or polypeptide. For example, a peripheral blood sample can be centrifugated to obtain an enriched cell sample. In addition, a cell sample can be treated such that total RNA is obtained. Once obtained, the total RNA can be evaluated to determine the amount of an IFN-γ-responsive mRNA present. Alternatively, a cell sample can be treated such that a polypeptide preparation is obtained. Once obtained, the polypeptide preparation can be evaluated to determine the amount of an IFN-γ-responsive polypeptide present.

Any method can be used to determine the level of an IFN-γ-responsive mRNA present within a sample. For example, the level of an IFN-γ-responsive mRNA present within a sample can be determined using PCR-based methods such as RT-PCR (e.g., quantitative RT-PCR and semi-quantitative RT-PCR) or northern blot analysis. The amount of IFN-γ-responsive mRNA present in a sample can be determined from an amplification reaction by fluorimetry or spectrophotometry. In addition, amplification products can be separated by gel electrophoresis and quantitated using a densitometer. The following procedure can be used to determine the level of IP-10 mRNA present within a sample. Briefly, a cellular sample can be obtained from an angina patient. Once obtained, the sample can be treated so that an RNA sample (e.g., mRNA or total RNA sample) is isolated. Any method can be used to isolate an RNA sample from any amount of cells (e.g., $1\times10^6$ cells). Once isolated, the RNA samples can be used with primers specific for IP-10 RNA in a PCR to amplify an IP-10 specific product. After completing the PCR, the level of IP-10 RNA can be determined.

Any method can be used to determine the level of an IFN-γ-responsive polypeptide present within a sample. For example, the level of an IFN-γ-responsive polypeptide present within a sample can be determined using polypeptide detection methods such as western blot analysis and immunochemistry (e.g., immunocyto-chemistry). The following procedure can be used to determine the level of CD64 or IP-10 polypeptide present within a sample. Briefly, a cellular sample can be obtained from an angina patient. Once obtained, the sample can be treated so that a polypeptide sample is isolated. Any method can be used to isolate a polypeptide sample from any amount of cells (e.g., $1\times10^6$ cells). Once isolated, the polypeptide sample can be stained with an antibody specific for CD64 or IP-10 polypeptide. Such antibodies can be labeled with any appropriate label such as a fluorescent, calorimeter, or radioactive molecule. After staining, the level of CD64 or IP-10 polypeptide can be determined.

In addition, fluorescent activated cell sorting (FACS) analysis can be used to determine the level of an IFN-γ-responsive polypeptide present within a sample. For example, a cell sample can be obtained and stained with anti-CD64 antibodies such that the number of cells expressing CD64 is determined or such that the amount of CD64 expressed by CD64$^+$ cells is determined. In this case, the level of an IFN-γ-responsive polypeptide present within a sample is determined by evaluating the number of cells expressing the IFN-γ-responsive polypeptide. In other words, comparing the number of IFN-γ-responsive polypeptide-expressing cells (e.g., percent of cells positive) within samples can be used to determine whether or not a particular sample contains an elevated level of an IFN-γ-responsive polypeptide.

3. Kits

The invention also provides kits that can be used to measure the level of an IFN-γ-activated transcription factor, the level of an IFN-γ-responsive mRNA, or the level of an IFN-γ-responsive polypeptide. Such kits can include two or more antibodies such that at least two different polypeptides (e.g., STAT-1, CD64, IP-10, and CD161) can be detected. Alternatively, such kits can contain at least two pairs of oligonucleotide primers such that at least two different target sequences can be amplified during an amplification reaction. Typically, the target sequence is a sequence present with an IFN-γ-responsive mRNA. The kits provided herein also can contain (1) a reference chart that indicates a reference level, (2) a positive control sample, and (3) a negative control sample. The positive control sample can be a sample that contains a known amount of a particular IFN-γ-responsive polypeptide, while the negative control sample can be a sample that lacks that particular IFN-γ-responsive polypeptide. The kits can be configured in any type of design (e.g., microtiter plate design) and can be made of any type of material (e.g., plastic).

4. Clonally Expanded T cells

The invention also provides substantially pure populations of CD28$^{null}$ T cells. The term "substantially pure population of CD28$^{null}$ T cells" as used herein refers to a collection of CD28$^{null}$ T cells that are separated from other types of cells (e.g., B cells, macrophages, and CD28$^+$ T cells) such that the CD28$^{null}$ T cells represent at least about 85 percent (e.g., at least about 90, 95, 99, or 100 percent) of all the cells of that collection. Each CD28$^{null}$ T cell within a substantially pure population can have a T-cell receptor that is present on a CD28$^{null}$ T cell expanded in an unstable angina patient. In addition, the CD28$^{null}$ T cells can be CD4 T cells or CD8 T cells and can express IFN-γ, perforin, and/or CD161.

Any method can be used to obtain a substantially pure population of CD28$^{null}$ T cells. For example, a cell sample can be obtained and stained with antibodies that identify T cells as well as CD28$^+$ T cells (e.g., anti-CD3, anti-CD4, anti-CD8, and anti-CD28 antibodies). Once stained, the cell sample can be sorted to isolate a T cell population that lacks CD28 expression. In addition, any method can be used to obtain a substantially pure population of CD28$^{null}$ T cells where the CD28$^{null}$ T cells have T-cell receptors that are present on CD28$^{null}$ T cells expanded in an unstable angina patient. For example, individual T cell clones obtained from an unstable angina patient can be screened to identify their particular T cell receptor sequences. Once obtained, the T cell receptor sequences can be compared to the T cell receptor sequences of clonally expanded CD28$^{null}$ T cells from an unstable angina patient.

Substantially pure populations of CD28$^{null}$ T cells having T-cell receptors that are present on CD28$^{null}$ T cells expanded in an unstable angina patient can be used to determine whether or not an antigen is an unstable angina antigen. An unstable angina antigen is any antigen that stimulates the clonal expansion of CD28$^{null}$ T cells in an unstable angina patient. Unstable angina antigens can be, without limitation, self polypeptides, bacterial polypeptides, viral polypeptides, fungal polypeptides, glycosylated polypeptides, lipids, and carbohydrates. An unstable angina antigen can be identified by (1) contacting a substantially pure population of CD28$^{null}$ T cells having T cell receptors that are present on CD28$^{null}$ T cells expanded in an unstable angina patient with antigen presenting cells (e.g., B cells, macrophages, dendritic cells) that were incubated with a potential antigen, and (2) determining whether or not that antigen stimulated any of the CD28$^{null}$ T cells. Antigens that stimulate the CD28$^{null}$ T cells are considered unstable angina antigens. Any method can be used to detect CD28$^{null}$ T cell stimulation. For example, proliferation or cytokine production can be measured to assess CD28$^{null}$ T cell stimulation.

The substantially pure populations of CD28$^{null}$ T cells provided herein can be used to identify compounds that inhibit CD28$^{null}$ T cell activation. For example, activated CD28$^{null}$ T cells can be contacted with a test compound. After contact, the CD28$^{null}$ T cells can be evaluated to determine whether or not the test compound reduced or eliminated CD28$^{null}$ T cell activation. Alternatively, unactivated CD28$^{null}$ T cells can be treated with a test compound. After or during treatment with the test compound, the unactivated CD28$^{null}$ T cells can be mixed with APC that were incubated with an unstable angina antigen (e.g., polypeptide preparation from unstable plaque tissue). After contact with the APC, the unactivated CD28$^{null}$ T cells can be evaluated to determine whether or not the test compound reduced or prevented the stimulation that is typically observed after contact with an APC presenting an unstable angina antigen.

5. Assisting Professionals

The methods and materials provided herein can be used to assist medical and research professionals in determining (1) whether or not a mammal contains at least one unstable plaque and/or (2) whether or not the mammal has an increased risk for developing an unstable plaque. In the case of a mammal with an angina condition, the methods and materials provided herein can be used to assist medical and research professionals in determining whether or not the angina condition is stable or unstable. Examples of medical professionals include, without limitation, doctors, nurses, laboratory technologists, and pharmacists. Examples of research professionals include, without limitation, scientists, technicians, and students. A professional can be assisted by (1) determining the level of an IFN-γ-activated transcription factor, the level of an IFN-γ-responsive mRNA, or an IFN-γ-responsive polypeptide in a sample, and (2) communicating information about one or more of those levels to that professional.

Typically, the communicated information will be the level of an IFN-γ-activated transcription factor, the level of an IFN-γ-responsive mRNA, or an IFN-γ-responsive polypeptide detected in a sample. The information, however, can be about whether or not a particular level is elevated. For example, a laboratory determining the level of an IFN-γ-responsive polypeptide can communicate information to a professional by simply telling the professional that the level of that IFN-γ-responsive polypeptide is greater than normal.

Any method can be used to communicate information to a professional. For example, the information can be given directly or indirectly to the professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information.

The invention will be further described in the following examples, which do not limit the scope of the invention described in the claims.

EXAMPLES

Example 1

IP-10 mRNA Levels are Elevated in UA Patients

IP-10 mRNA levels in peripheral blood mononuclear cells (PBMC) from stable angina (SA) patients, unstable angina (UA) patients, and healthy age-matched controls were measured. The SA patients had no acute events or worsening of symptoms during the prior six months. In addition, the SA patients had no angina episodes the week prior to analysis. The UA patients had, during 48 hours prior to analysis, either at least two episodes of angina at rest or one episode lasting more than 20 minutes. In addition, the UA patients had an ST segment shift diagnostic for myocardial ischemia during the angina episode or episodes. Further, the UA patients had no elevation in serum creatinine kinase levels on admission and during the first 24 hours of hospitalization. Patients with acute or chronic inflammatory diseases as well as patients having had myocardial infarction, angioplasty, or heart failure within the previous six months were excluded.

RT-PCR was used to measure IP-10 mRNA levels from PBMC freshly harvested from SA patients, UA patients, and healthy controls. Briefly, blood samples were drawn upon hospital admission. Once the PBMC were collected, total RNA was extracted from about $5 \times 10^5$ PBMC using a TriZol kit (Life Technologies, Grand Island, N.Y.). To amplify IP-10-specific sequences corresponding to IP-10 mRNA, IP-10 primers were designed. The sequence of the forward primer was as follows: 5'-GGAACCTCCAGTCTCAGCACC-3'(SEQ ID NO: 2). The sequence of the reverse primer was as follows: 5'-CAGCCTCTGTGTGGTCCATCC-3'(SEQ ID NO: 3). The IP-10 sequence is provided at GenBank accession number NM_001565. PBMC ($5 \times 10^5$) stimulated for 90 minutes with IFN-γ(100 U/mL, 500 U/mL, or 1000 U/mL) were used as a positive control for the IP-10 RT-PCR reactions. β-actin-specific primers were used as a general control for the amplication reactions. The sequence of the forward β-actin-specific primer was as follows: 5'-ATCATGTTTGAGACCTTCAACACCCC-3'(SEQ ID NO: 4). The sequence of the reverse β-actin-specific primer was as follows: 5'-CAGGAGGAGCAATGATCTTGAT-3' (SEQ ID NO: 5). The β-actin sequence is provided at GenBank accession number M10277 or NM_001101. Each amplification reaction had 22 cycles and was performed using an annealing temperature of 64° C.

A strong amplification product corresponding to IP-10 was detected in samples from 18 of the 22 UA patients and 3 of the 20 SA patients (P<0.001; Fisher Exact Test). No IP-10-specific amplification products were detected in samples from healthy controls. IP-10-specific amplification products, however, were detected from PBMC cultured with 1000 U/mL of IFN-γ. The intensity of the amplification products from the PBMC cultured with 1000 U/mL of IFN-γ was equivalent to that observed for the samples freshly isolated from UA patients. Thus, the level of IP-10 mRNA detected in PBMC collected from angina patients can be used to distinguish unstable angina from stable angina.

Eight of 27 UA patients had elevated troponin levels (≧2.0 ng/mL), indicating that these eight UA patients have myonecrosis. A comparison of the IP-10 mRNA levels from these eight UA patients with the IP-10 mRNA levels from the 19 troponin-negative UA patients did not show any difference. Thus, myonecrosis does not appear to be a major determinant in inducing IP-10 expression.

Example 2

CD64 Expression Levels are Elevated in Circulating Monocytes from UA Patients

The level of CD64 expression in monocytes from SA patients, UA patients, and age-matched controls were compared. PBMC from blood samples were enriched for monocytes using a negative selection procedure designed to avoid artificial activation of monocytes. Briefly, each sample was enriched for monocytes using the No-Touch Monocyte Isolation Kit (Miltenyi Biotec, Auburn, Calif.) with a column exposed to a magnetic field (VarioMACS, Miltenyi Biotec).

Once obtained, each monocyte-enriched sample was stained with FITC-conjugated anti-CD64 monoclonal antibodies (BeckmanCoulter, Miami, Fla.) as well as PE-conjugated anti-CD14 monoclonal antibodies (Becton Dickinson). The anti-CD14 antibodies were used to identify CD14+ monocytes while the anti-CD64 antibodies were used to assess the level of CD64 expression by CD14+ cells. The stained cells were analyzed on a FACSCalibur® flow cytometer (Becton Dickinson), and the level of CD64 expression quantified.

The level of CD64 expression by CD14+ cells from SA patients (median fluorescence intensity 71.8) was indistinguishable from the level of CD64 expression by CD14+ cells from healthy age-matched controls (median fluorescence intensity 67.4; FIG. 1). In contrast, the level of CD64 expression by CD14+ cells from UA patients (median fluorescence intensity 105.1) was significantly higher than the level of CD64 expression observed in CD14+ cells from either SA patients (P=0.003) or healthy age-matched controls (P=0.008; One-way ANOVA; FIG. 1).

These results demonstrate that circulating monocytes from UA patients are activated and express an elevated level of CD64 expression that is detectable, indicating that the level of CD64 expression can be used to distinguish UA patients from SA patients and healthy controls.

Example 3

Monocytes from UA Patients are Hyper-responsive to IFN-γ

PBMC samples isolated from SA patients, UA patients, and healthy age-matched controls were enriched for monocytes as described in Example 2. Once enriched, each sample was tested to determine the level of IFN-γ responsiveness exhibited by the monocytes. Briefly, about $1 \times 10^6$ cells from each sample were incubated at 37° C. with or without 200 U/mL of IFN-γ (BioSource International, Camarillo, Calif.), the optimal IFN-γ concentration determined using titration experiments. After incubation, the level of CD64 expression was assessed as described in Example 2.

Figure 2:
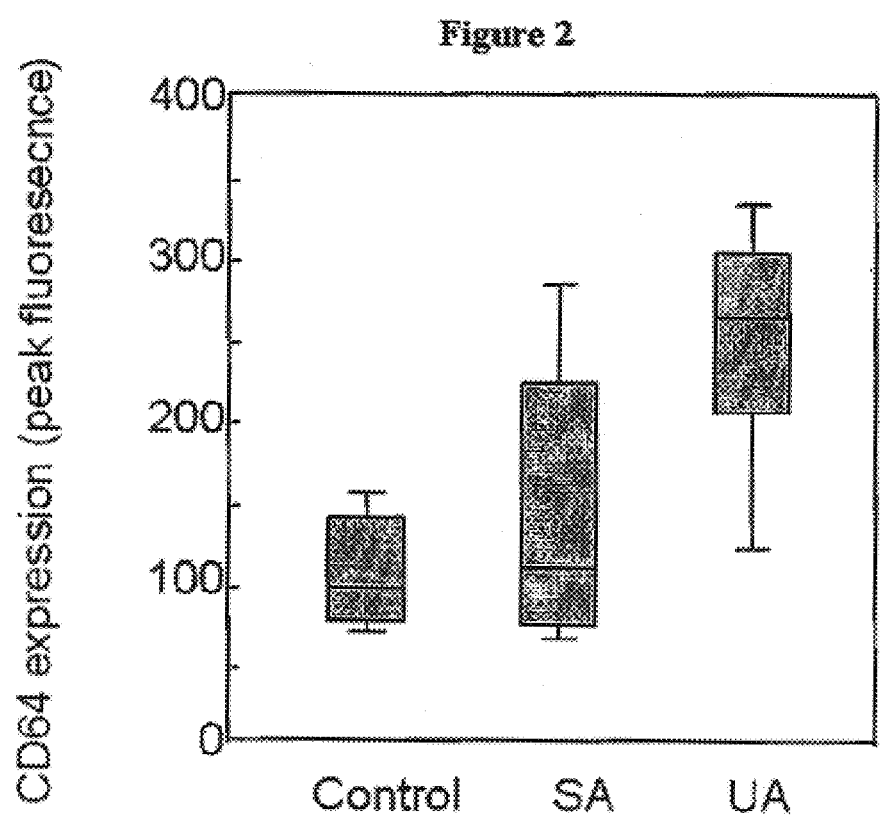
FIG. 2 is a bar graph plotting CD64 expression levels of samples from healthy controls, SA patients, and UA patients that were treated in vitro with IFN-γ. The median value is represented as a line, the 25th and 75th percentiles are represented as boxes, and the 10th and 90th percentiles are represented as whiskers.

IFN-γ induced CD64 expression rapidly with maximal surface expression levels being detected after about 12 to 18 hours of incubation with IFN-γ. After an 18 hour incubation with IFN-γ, monocyte-enriched samples from SA patients and healthy age-matched controls were found to contain monocytes that exhibited a prompt increase in CD64 surface expression. The median fluorescence intensity observed for monocytes from SA patients increased to 99.9, while the median fluorescence intensity observed for monocytes from healthy age-matched controls increased to 112.5 (FIG. 2). These fluorescence levels are equivalent to the levels detected in untreated monocytes obtained from UA patients (FIG. 1). After an 18 hour incubation with IFN-γ, monocyte-enriched samples from UA patients also were found to contain monocytes that exhibited a prompt increase in CD64 surface expression. In fact, the level of CD64 expression was found to increase more than a factor of two after IFN-γ treatment (median fluorescence intensity 266.6; FIG. 2). The differences in IFN-γ-induced CD64 expression were highly significant between samples from UA patients and SA patients (P=0.003) as well as between samples from UA patients and healthy age-matched controls (P<0.001).

Figure 3:
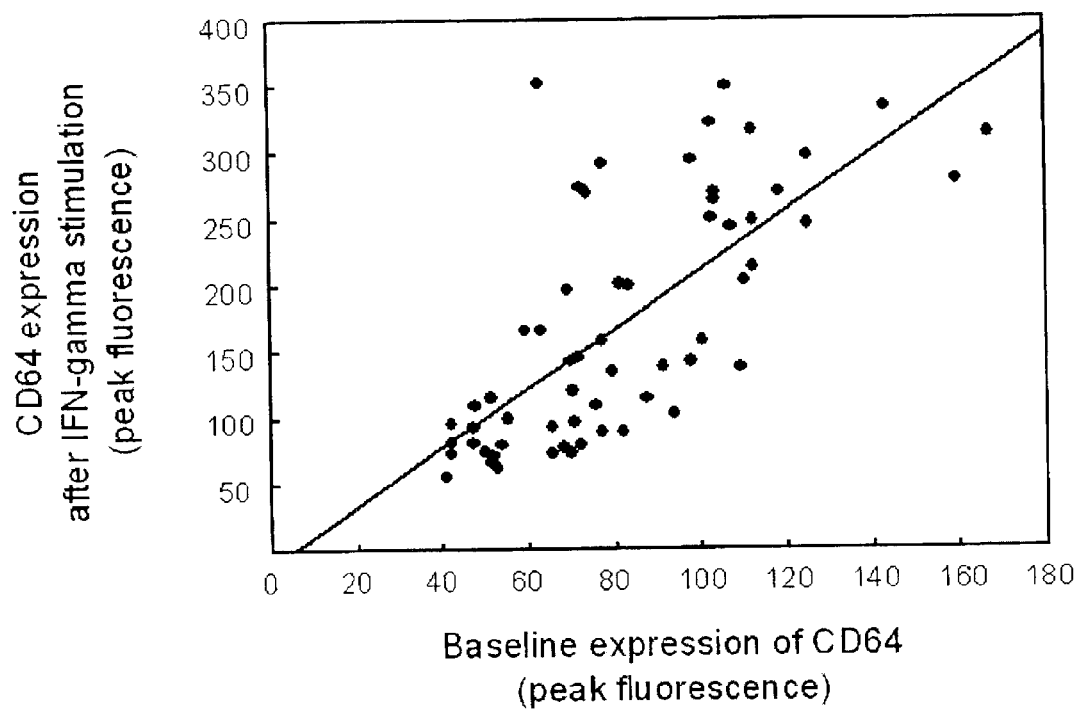
FIG. 3 is a graph plotting the correlation of spontaneous and IFN-γ-induced expression of CD64 by $CD14^+$ monocytes.

These results indicate that monocytes obtained from UA patients are not maximally stimulated at the time of isolation. These results also indicate that monocytes from UA patients received an initial in vivo IFN-γ induction of CD64 gene transcription that led to enhanced responsiveness of the CD64 promoter to re-exposure to in vitro IFN-γ. In fact, baseline CD64 levels were found to be strongly predictive of the increased surface expression of CD64 induced by in vitro IFN-γ treatment (FIG. 3). Thus, UA patients have monocytes with an elevated baseline level of CD64 expression as well as monocytes with an enhanced responsiveness to IFN-γ treatment when compared to monocytes from SA patients or healthy controls.

Eight of 27 UA patients had elevated troponin levels (≧2.0 ng/mL), indicating that these eight UA patients have myonecrosis. A comparison of the level of CD64 expression by monocytes from these eight UA patients with the level of CD64 expression by monocytes from the 19 troponin-negative UA patients did not show any difference. Thus, myonecrosis does not appear to be a major determinant in inducing CD64 expression.

Example 4

STAT-1 is Found in the Nuclei of Monocytes from UA Patients

PBMC and monocyte-enriched samples from SA patients, UA patients, and healthy age-matched controls were prepared as described in Example 2. A high salt extraction protocol was used to obtain nuclear extracts from about $1 \times 10^7$ cells from the PBMC samples or from about $1 \times 10^6$ cells from the monocyte-enriched samples. Once isolated, each nuclear extract was analyzed using an electrophoretic mobility shift assay as described elsewhere (Vallejo et al., *J. Biol. Chem.*, 273:8119–8129 (1998)). Briefly, an aliquot (about 5 μg protein) of each nuclear extract was added to 15 μL of binding buffer, 1.5 mg of poly(dI-dC) (Sigma Chemical Co, St Louis, Mo.), and 1.5 mg of a double-stranded oligonucleotide probe containing a sis-inducible element (SIE oligonucleotide; 5'-CGCCATTTCCCGTAAATC-3'; SEQ ID NO: 1). A nonspecific oligonucleotide probe (1.5 mg) was used as a control. This nonspecific oligonucleotide had the following sequence: 5'-TCGAAGTACTCAATTGCTCGAGATCGATAG-ATCTGAATTCAGTACTCC-3'(SEQ ID NO: 6). Each probe was radiolabeled with [γ-$^{32}$P]ATP (NEN, Boston, Mass.) using a standard end-labeling reaction. Once annealed, the probes were added to the appropriate reactions at a final concentration of 40 fmol/mL. After adding the probes, each reaction was incubated at room temperature for 30 minutes. Protein-DNA complexes were resolved on 6 percent non-denaturing polyacrylamide gels and detected by autoradiography. A nuclear extract prepared from $1 \times 10^7$ PBMC incubated for 30 minutes with 500 U/mL IFN-γ was used as a positive control.

Figure 4:
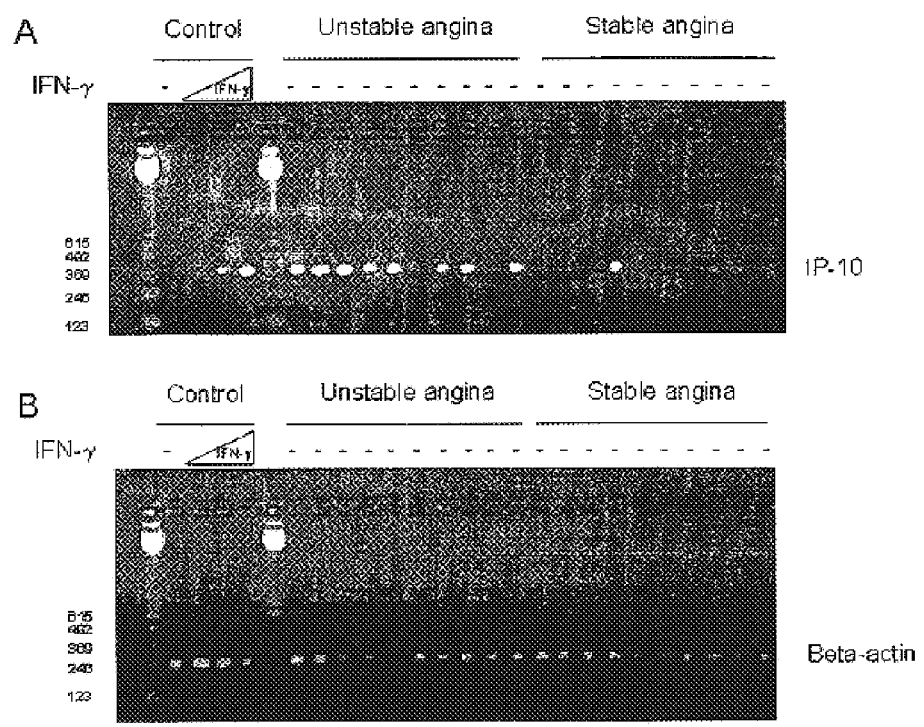
FIG. 4 contains two photographs of electrophoresis gels. The samples and bands corresponding to IP-10 (photograph A) and β-actin (photograph B) are indicated.

Radioactive SIE probes from reactions containing nuclear extracts prepared using PBMC from SA patients exhibited the same gel electrophoretic mobility as radioactive SIE probes that were not incubated with nuclear extracts. Radioactive SIE probes from reactions containing nuclear extracts prepared using PBMC from UA patients, however, exhibited reduced gel electrophoretic mobility. Specifically, nuclear extracts from 9 of 12 UA patients were found to reduce the gel electrophoretic mobility of the SIE probe, while none the nuclear extracts from the 11 SA patients analyzed were found to reduce the gel electrophoretic mobility of the SIE probe (FIG. 4). No gel shift was observed for the radioactive nonspecific probe when incubated with the nuclear extracts. In addition, the gel shift observed for the reactions containing nuclear extracts prepared using cells from UA patients was similar to that observed for the positive control (SIE probe incubated with a nuclear extract prepared from PBMC treated with IFN-γ).

To confirm that the gel shift observed for reactions containing nuclear extracts prepared using PBMC from UA patients was the result of activated STAT-1 interacting with the radioactive SIE probe, a super shift assay was performed. Briefly, 1 μg of a STAT-1α-specific antibody (Transduction Laboratories, Lexington, Ky.) or irrelevant mouse IgG1 antibody (Sigma) was added to reaction mixtures containing the radioactive SIE probe and nuclear extract. Once added, each reaction mixture was adjusted to 25 μL and incubated on ice for 30 minutes.

Figure 5:
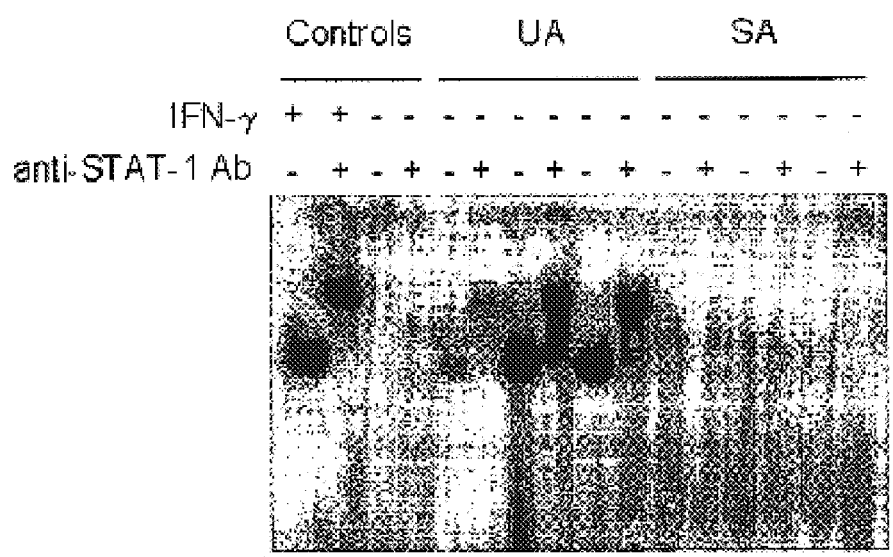
FIG. 5 is a photograph of an electrophoresis gel from a super shift assay. The samples and treatments are indicated.

The addition of the STAT-1α-specific antibody to the reactions containing nuclear extracts that (1) were prepared using PBMC from UA patients and (2) found to reduce the gel electrophoretic mobility of the SIE probe resulted in a further reduction in the gel electrophoretic mobility of the SIE probe (FIG. 5). The observed shift in band migration was almost complete indicating that the complexes consisted mostly, if not entirely, of STAT-1α homodimers complexed with the SIE probe.

To identify the cell population that contained the activated STAT-1 responsible for the observed gel shift, monocyte-enriched samples were prepared from the PBMC samples and analyzed. Nuclear extracts prepared from monocyte-enriched samples yielded results identical to those obtained using nuclear extracts prepared from the unseparated PBMC samples.

These results demonstrate that UA patients have circulating monocytes that were previously exposed to and activated by IFN-γ in vivo. These results also demonstrate that the presence or absence of STAT-1 in nuclear extracts can be used to distinguish UA patients from SA patients and healthy controls.

Example 6

CD4$^+$CD28$^+$ T cells are Expanded Clonally in UA Patients

A FACSVantage® flow cytometer was used to sort CD4$^+$ CD28$^{null}$ and CD4$^+$CD28$^{null}$ T cells from PBMC samples obtained from 20 UA patients. After obtaining the CD4$^+$ CD28+ and CD4+CD28+ T cells from each sample, total RNA was extracted. Briefly, a Trizol kit (Life Technologies, Grand Island, N.Y.) was used to isolate total RNA from 1×10⁵ CD4+CD28+ cells or from 1×10⁵ CD4+CD28+ cells. Once obtained, the total RNA was used in amplification reactions with a BC-specific primer as well as primers specific for BV2, BV3, BV5S2, BV6, BV7, BV8, BV13S1, BV14, BV17, and BV18 as described elsewhere (Waase et al., *Arthritis Rheum.* 39:904–913 (1996) and Choi et al., *Proc. Nat'l. Acad. Sci. USA* 86:8941–8945 (1989)). The BV families analyzed cover about 50 percent of a person's total TCR repertoire. A primer extension assay with T4 kinase was used to end-label the BC primer.

After conducting RT-PCR, the amplification products were separated on a 5 percent denaturing polyacrylamide gel. Band intensities were analyzed to determine whether the distribution was Gaussian or skewed by dominant bands. A Gaussian distribution indicates that the T cell population is polyclonal, while the presence of dominant bands indicates that that subset of the T cell population was clonally expanded. Typically, bands with intensities greater than the sum of two adjacent bands and accounting for at least about 30 percent of the total observed amplification product are predictive of clonality. Observed dominant bands were directly sequenced by automated sequencing (ABI Prism® Sequence Detection System, Perkin Elmer Applied Biosystems, Foster City, Calif.).

Figure 6:
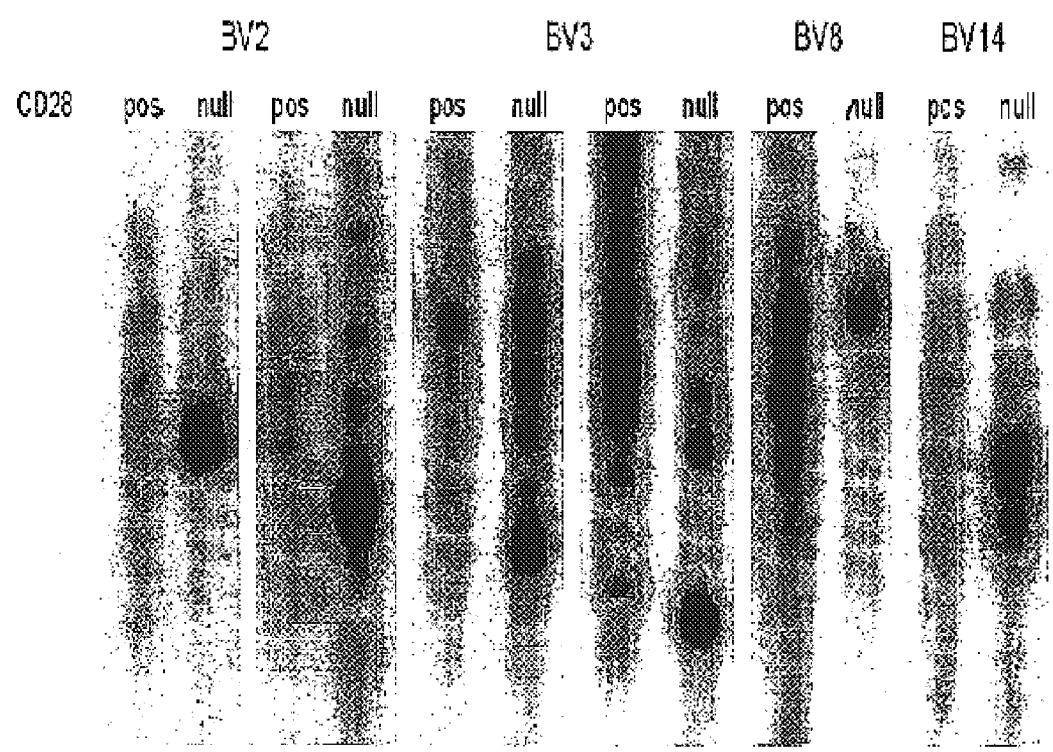
FIG. 6 is a series of photographs of electrophoresis gels from amplification reactions using total RNA samples from either $CD4^+CD28^+$ T cells (pos) or $CD4^+CD28^{null}$ T cells (null).

The distribution of amplification products from the reactions containing total RNA from CD4+CD28+ T cells followed a Gaussian distribution. In contrast, the distribution of amplification products from the reactions containing total RNA from CD4+CD28$^{null}$ T cells frequently deviated from a Gaussian distribution (FIG. 6).

Seventy-two dominant bands amplified from the total RNA of CD4+CD28$^{null}$ T cells from UA patients were sequenced. Fifty-nine of the 72 dominant bands yielded unequivocal sequences that confirmed the presence of clonal T cell populations. Specifically, an average of three T cell clones was observed for each UA patient (range 0–11). Since the primer sets used cover about 50 percent of the CD4+ T cell repertoire, it is estimated that an UA patient has an average of six clonally expanded CD4+ T cells. In addition, individual T cell clones were found to have varying degrees of expansion ranging from slightly expanded (accounting for about 0.5 percent of the T cell repertoire) to greatly expanded (accounting for as mush as five percent of the T cell repertoire). It is noted that one UA patient lacked clonal TCR sequences and also had a lower frequency of CD4+ CD28$^{null}$ T cells. A comparison of clinical parameters between UA patients with low and high numbers of T cell clonotypes demonstrated no features correlating with the extent of oligoclonality. These results indicate that UA patients have clonally expanded CD4+CD28$^{null}$ T cells.

Example 7

Clonally Expanded CD4+CD28$^{null}$ T cells are Stable in UA Patients

Figure 7:
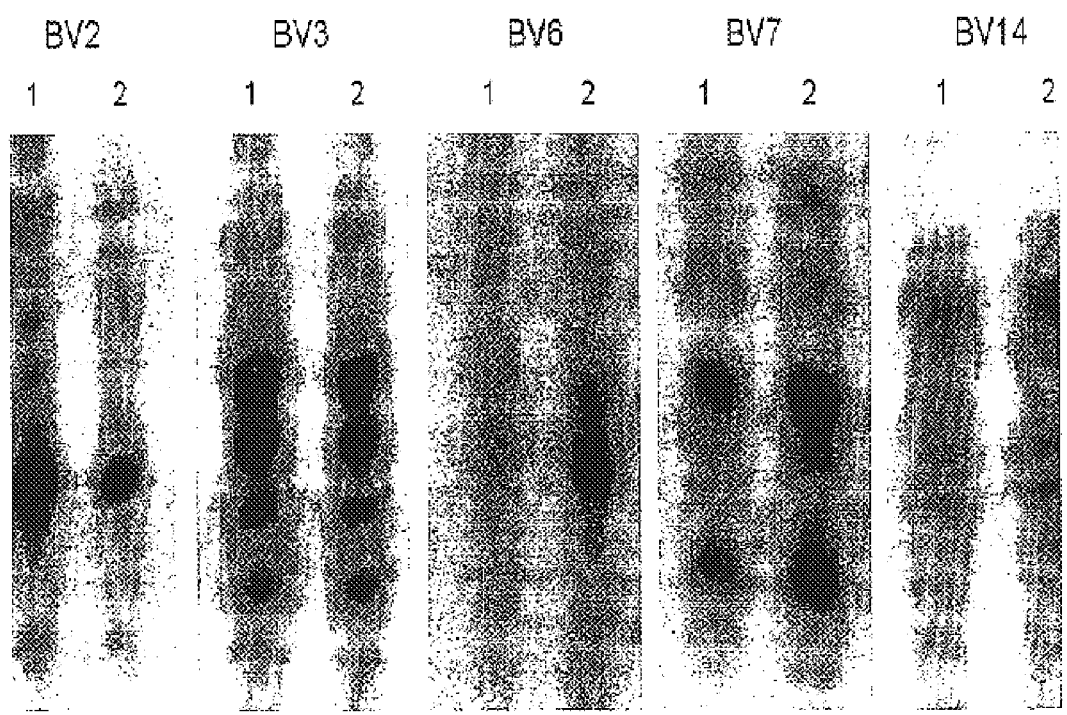
FIG. 7 is a series of photographs of electrophoresis gels from amplification reactions using total RNA samples from $CD4^+CD28^+$ T cells collected from five patients either initially (1) or six months later (2).

Five UA patients were analyzed as described in Example 6. Six months after this analysis, peripheral blood CD4+ CD28$^{null}$ T cells were obtained from those five patients and reanalyzed. Clonal dominance by selected T cells in the CD4+CD28$^{null}$ T-cell compartment was found to be maintained for the majority (16 of 18) of expanded clonotypes (FIG. 7). The clonal identity of these clonotypes was confirmed by sequencing.

Example 8

Analysis of the Clonally Expanded T cell in UA Patients

Figure 8:
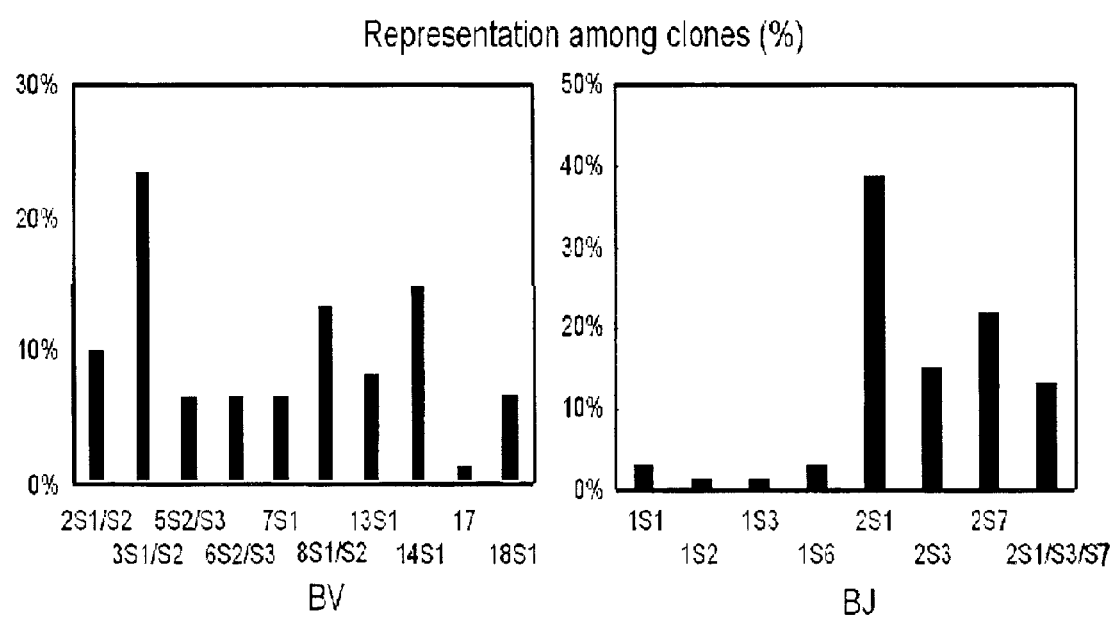
FIG. 8 contains two bar graphs plotting the percentage of representation among clones for the indicated TCR-BV and TCR-BJ gene segments.

The sequences of the 59 amplified products sequenced in Example 6 were analyzed to determine the usage of TCR-BV and TCR-BJ gene segments between UA patients (FIG. 8). The distribution of BV gene segments from clonally expanded T cells was different from that of unselected T cell populations with the most common BV element (BV3S1/S2) accounting for about 24 percent of all expanded clonotypes. The expected percentage for this element in a sample obtained from a healthy person selected at random is 5 percent. In addition, BV14S1 and BV8S1/S2 segments were frequently detected among the UA patients, while BV17 and BV6S2/S3 segments were detected in only a small proportion of clonal T cells.

Non-random use of TCR gene segments was even more pronounced for BJ genes. More than 35 percent of the amplified sequences contained a rearranged BJ2S1 gene segment, while more than 22 percent of the amplified sequences contained a rearranged BJ2S7 gene segment. More than 15 percent of the amplified sequences contained a rearranged BJ2S3 gene segment. BJ2S2 and BJ2S5 gene segments were not detected, and BJ gene segments of the BJ1 family were detected infrequently. The BV3S1/S2-BJ2S1 TCR gene segment combination was detected in about 11 percent of the sequence compared to an expected one percent frequency in a random T cell population. These results indicate that the observed clonal expansion of CD4+ CD28$^{null}$ T cells in UA patients could be triggered by a common antigen or common set of antigens.

The junctional N-D-N region at the interface of TCR-BV and -BJ gene segments directly contacts the antigenic peptide. The nucleotide and amino acid sequences at this junctional region for the different expanded clonotypes were compared. Receptor homology was defined as the sharing of at least about 60 percent of the amino acid sequence. Of the 59 sequences analyzed, similarities were observed in ten sequences from samples obtained from seven UA patients (Table 1). One UA patient was found to have two clonotypes and another found to have three clonotypes that expressed N-D-N sequences very similar to those sequences identified in a third UA patient. The group of related TCR sequences included three receptors having the overrepresented BV3S1/S2-BJ2S1 rearrangement. All the sequences with shared amino acid sequence homology displayed heterogeneity at the nucleotide level.

TABLE 1

Amino acid sequence homologies of TCR β-chains from expanded clonotypes derived from different patients with UA.

| Donor | BV | N-D-N | BJ |
|---|---|---|---|
| BE | 3S1/S2 CASS | L G [G G T Y]<br>tta gga ggg ggc acc tat | EQFF 2S1<br>(SEQ ID NO:10)<br>(SEQ ID NO:11) |
| LM | 3S1/S2 CASS | P T [G G T Y]<br>ccc acc ggg ggg acc tat | EQFF 2S1<br>(SEQ ID NO:12)<br>(SEQ ID NO:13) |

TABLE 1-continued

Amino acid sequence homologies of TCR β-chains from expanded clonotypes derived from different patients with UA.

| Donor | BV | N-D-N | BJ |
|---|---|---|---|
| RM | 3S1/S2 CASS | L G G G D Y<br>tta ggg ggg ggc gac tat | DQYF 2S3<br>(SEQ ID NO:14)<br>(SEQ ID NO:15) |
| SW | 3S1/S2 CASS | S G G G T Y<br>agc ggc ggg ggc acc tat | EQFF 2S1<br>(SEQ ID NO:16)<br>(SEQ ID NO:17) |
| LM | 7S1 CASS | R E G T E G S Y<br>cgc gaa gga acg gaa ggg tcc tat | EQYF 2S7<br>(SEQ ID NO:18)<br>(SEQ ID NO:19) |
| UA | 7S1 CASS | R E G G G S Y<br>cgc gaa ggg ggg ggg tcc tat | EQYF 2S7<br>(SEQ ID NO:20)<br>(SEQ ID NO:21) |
| BL | 8S1/S2 CASS | S S R G D Y<br>agc agc agg ggc gac tat | EQYF 2S7<br>(SEQ ID NO:22)<br>(SEQ ID NO:23) |
| UA | 8S1/S2 CASS | S S R G T H<br>agc agt agg ggg acc cat | EQFF 2S1<br>(SEQ ID NO:24)<br>(SEQ ID NO:25) |
| UA | 14S1 CASS | F G A S Y<br>ttc ggg gcc tcc tat | EQYF 2S7<br>(SEQ ID NO:26)<br>(SEQ ID NO:27) |
| WE | 14S1 CASS | Y G A S Y<br>tac ggt gcc tcc tat | EQYF 2S7<br>(SEQ ID NO:28)<br>(SEQ ID NO:29) |

Example 9

Clonally Expanded CD4+CD28$^{null}$ T cells are Present in Unstable Plaques

A PBMC sample was obtained from a patient that had a fatal myocardial infarction in the territory of the right coronary artery (RCA). In addition, coronary artery specimens were obtained from the left anterior descending (LAD) and the RCA of this patient. The arterial fragments were confirmed to contain stable and unstable plaques by histology. In addition, a sample with a fissured plaque was obtained from a patient undergoing atherectomy. The culprit (unstable plaques) and nonculprit (stable plaques) lesions were examined to determine whether clonally expanded CD4+CD28$^{null}$ T cells were present within the lesions. Briefly, total RNA was extracted from the unstable plaque samples and from the stable plaque samples. Once obtained, the total RNA was used in amplification reactions with a BC anti-sense primer (5'-CTGTGCACCTCCTTCCCATTC-3' SEQ ID NO: 7) and BV specific primers as well as a nested set of BC primers (5'-GTGGGAGATCTCTGCTTCTG-3' SEQ ID NO: 8 and 5'-TTCTGATGGCTCAAACAC-3' SEQ ID NO: 9). The amplification products were sequenced.

Figure 9:
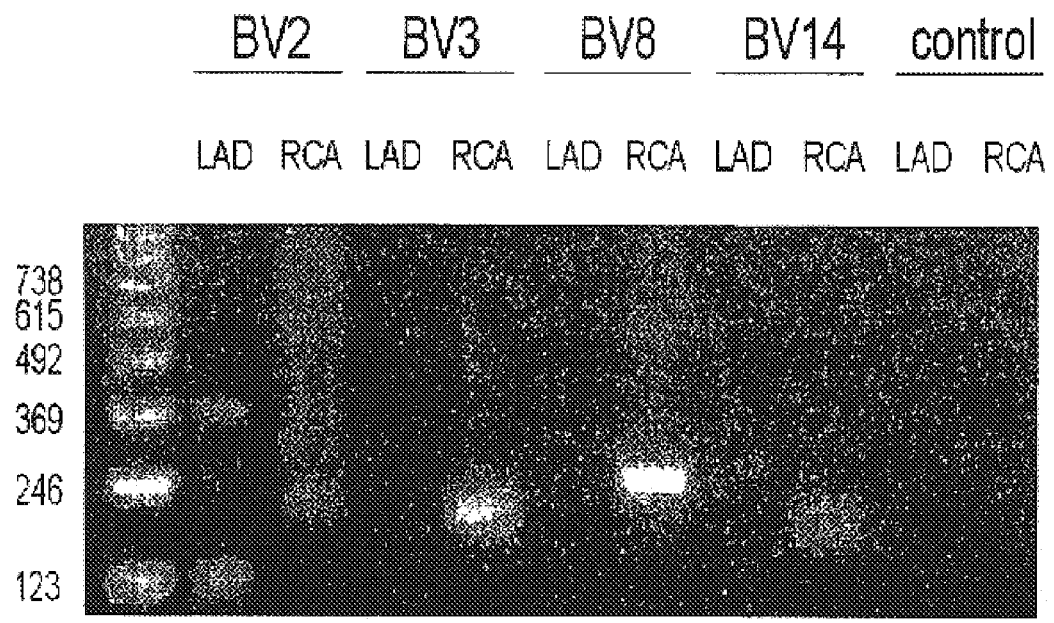
FIG. 9 is a photograph of an electrophoresis gel of amplification reactions using primers specific for the indicated TCR gene segments and RNA from either LAD or RCA samples.

Analysis of the PBMC obtained from the patient having had a fatal myocardial infarction revealed that CD4+ CD28$^{null}$ T cells were highly expanded and included five clonal TCR sequences (Table 2). Analysis of the plaque tissue revealed that no tissue-infiltrating T cells were detected in the coronary artery tissue from a stable plaque. Tissue-infiltrating T cells, however, were detected in the arterial wall segment of the lesion that caused the fatal myocardial infarction (FIG. 9). Two (a BV3+ clone and a BV8+ clone) of the five sequences identified in the peripheral blood were detected in the unstable plaque tissue. In fact, those two clones were dominant clones in the culprit tissue. In addition, a clonal BV14+ TCR sequence was found in the culprit tissue sample. This clonal BV14+ sequence, however, was distinct from the sequence of the expanded BV14+ clones detected in the periphery. BV2+ T cells displayed polyclonal receptors in the tissue. Analysis of the samples from the second patient revealed similar findings. In fact, unstable plaque tissue was found to contain two clonal T cell populations that had receptor sequences corresponding to sequences found in peripheral CD4+CD28$^{null}$ T cells (Table 3).

TABLE 2

Accumulation of selected CD4+CD28$^{null}$ T-cell clones in the unstable plaque of a patient who died from an acute myocardial infarction.

| | Peripheral blood | | Coronary artery tissue | |
|---|---|---|---|---|
| | CD4+CD28+ T cells | CD4+CD28$^{null}$ T cells | LAD | RCA |
| BV2S2 | Polyclonal | DPAGGAD BJ2S3<br>(SEQ ID NO:30) | nd | polyclonal |
| BV3S1/S2 | Polyclonal | SPAGTYN BJ2S1<br>(SEQ ID NO:31) | nd | SPAGTYN BJ2S1<br>(SEQ ID NO:31) |
| BV8S1/S2 | Polyclonal | SLGTTGN BJ1S3<br>(SEQ ID NO:32) | nd | SLGTTGN BJ1S3<br>(SEQ ID NO:32) |

TABLE 2-continued

Accumulation of selected CD4+CD28null T-cell clones in the unstable plaque of a patient who died from an acute myocardial infarction.

| | Peripheral blood | | Coronary artery tissue | |
| --- | --- | --- | --- | --- |
| | CD4+CD28+ T cells | CD4+CD28null T cells | LAD | RCA |
| BV14S1 | Polyclonal | LRDRES (SEQ ID NO:33) | BJ1S2 | nd | PTSED (SEQ ID NO:35) | BJ2S1 |
| | | RQGTY (SEQ ID NO:34) | BJ2S1/S3 | | |

LAD = left anterior descending coronary artery; RCA = right coronary artery; nd = not detected. Bold T-cell receptor sequences are from those clones that were expanded in the periphery as well as in the unstable plaque.

TABLE 3

T-cell receptor sequences detected in the unstable plaque obtained from a patient having had atherectomy.

| Peripheral blood | | |
| --- | --- | --- |
| CD4+CD28+T cells | CD4+CD28null T cells | Unstable plaque |
| polyclonal | BV3 ASSYNS BJ1S6 (SEQ ID NO:36) | BV3 ASSYNS BJ1S6 (SEQ ID NO:36) |
| polyclonal | BV18 PRQDT BJ1S1 (SEQ ID NO:37) | BV18 PRQDT BJ1S1 (SEQ ID NO:37) |

Example 10

CD40 is a Costimulatory Molecule for CD4+ CD28$^{null}$ T cells

Figure 10:
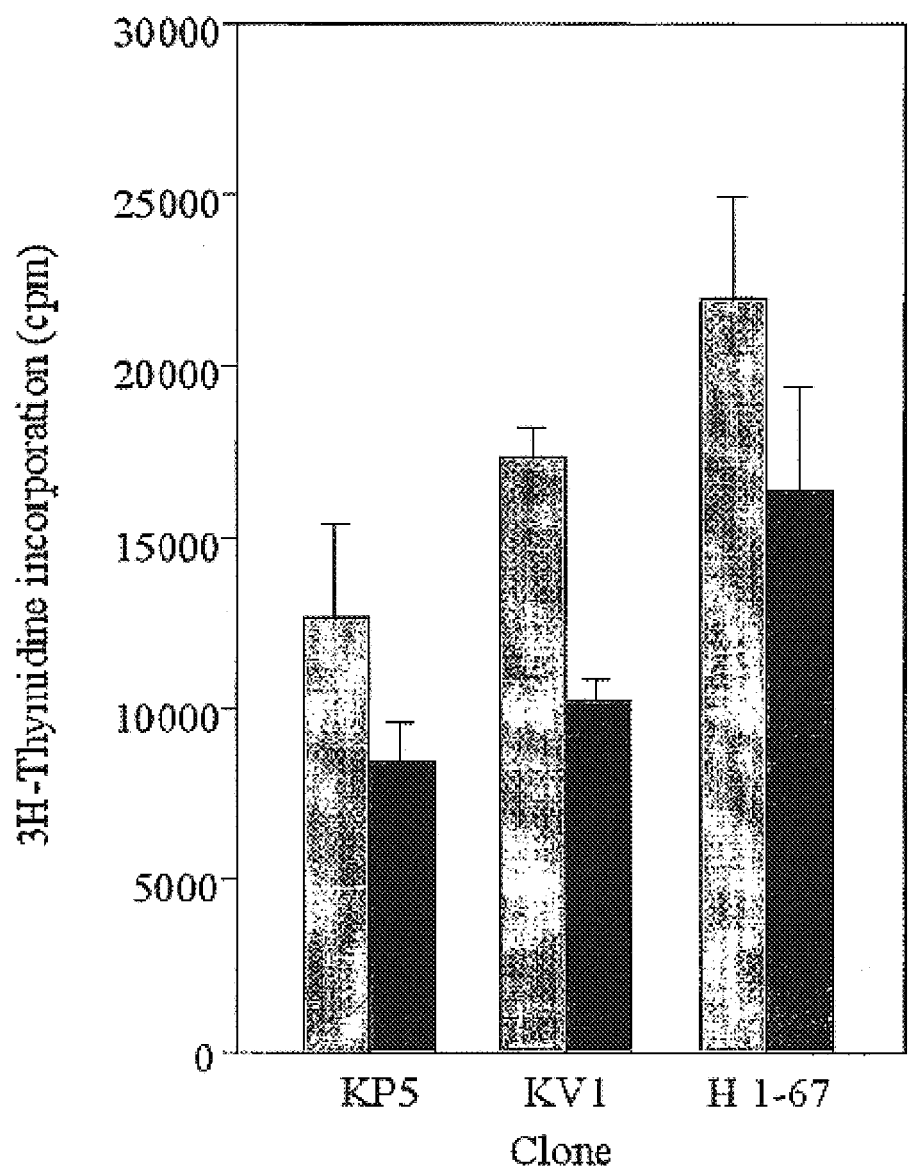
FIG. 10 is bar graph plotting the amount of thymidine incorporation for the indicated clones. The light-shaded bars indicate the amount of thymidine incorporation for cell treated with a control IgG antibody, while the dark-shaded bars indicate the amount of thymidine incorporation for cell treated with an anti-CD40 antibody.

CD4+CD28$^{null}$ T cells were exposed to anti-CD3 antibodies immobilized on monocytes and either an anti-CD40 monoclonal antibody or a control IgG antibody. After 72 hours, the level of proliferation was measured. The presence of 5 µg/mL of anti-CD40 antibody partially inhibited T-cell proliferation when compared to cells exposed to the control IgG antibody (FIG. 10). This result indicates that the CD40 molecule expressed by CD4+CD28$^{null}$ T cells can provide a stimulatory signal. This result also indicates that inhibitors of the CD40-CD40L interaction (e.g., anti-CD40 antibodies) can be used to reduce the stimulation of CD4+CD28$^{null}$ T cells. Since CD40L is expressed by vascular endothelial cells, smooth muscle cells, and macrophages in atherosclerotic plaques, inhibitors of the CD40-CD40L interaction can be used to reduce the stimulation of tissue-infiltrating CD4+CD28$^{null}$ T cells in plaques. Inhibiting the CD40-CD40L interaction can reduce the ability of CD4+CD28$^{null}$ T cells to lyse target cells and to induce apoptosis, which can lead to cap thinning and can favor plaque disruption.

Example 11

CD47 is a Costimulatory Molecule for CD4+ CD28$^{null}$ T cells

Figure 11:
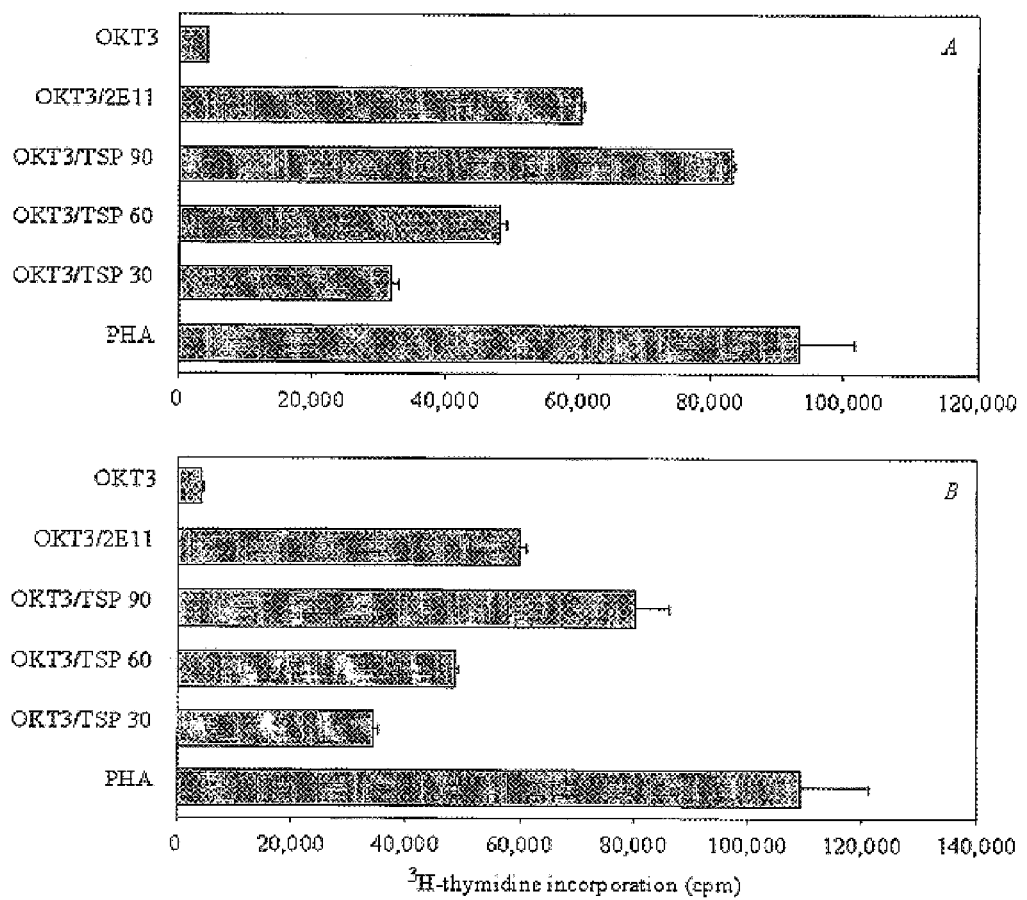
FIG. 11 contains two bar graphs plotting the amount of thymidine incorporation for $CD4^+CD28^{null}$ T cells exposed to the indicated treatments.

CD4+CD28$^{null}$ T cells were exposed a suboptimal concentration of anti-CD3 antibodies (100 ng/mL of OKT3) and either crosslinked anti-CD47 antibody (mAb 2E11) or varying concentrations of platelet-derived thrombospondin-1 (TSP-1). A lectin (PHA) was used as a positive control. After 72 hours of exposure, the level of proliferation was measured. Anti-CD47 antibody coated to plates boosted the level of proliferation observed for CD4+CD28$^{null}$ T cells treated with a suboptimal concentration of anti-CD3 antibodies. Likewise, TSP-1 boosted, in a dose-dependent fashion, the level of proliferation observed for CD4+CD28$^{null}$ T cells treated with a suboptimal concentration of anti-CD3 antibodies (FIG. 11). The addition of soluble anti-CD47 antibody to CD4+CD28$^{null}$ T cells treated with 90 µg/mL of TSP-1 and a suboptimal concentration of anti-CD3 antibodies blocked the level of proliferation induced by the TSP-1, suggesting that thromnbospondin delivers a costimulatory signal by binding to CD47. These results indicate that CD4+CD28$^{null}$ T cells can be stimulated by CD47 interactions. These results also indicate that blocking CD47 interactions can inhibit CD4+CD28$^{null}$ T cell stimulation.

Example 12

CD161 is a Marker for Activated CD4+CD28$^{null}$ T cells

Figure 12:
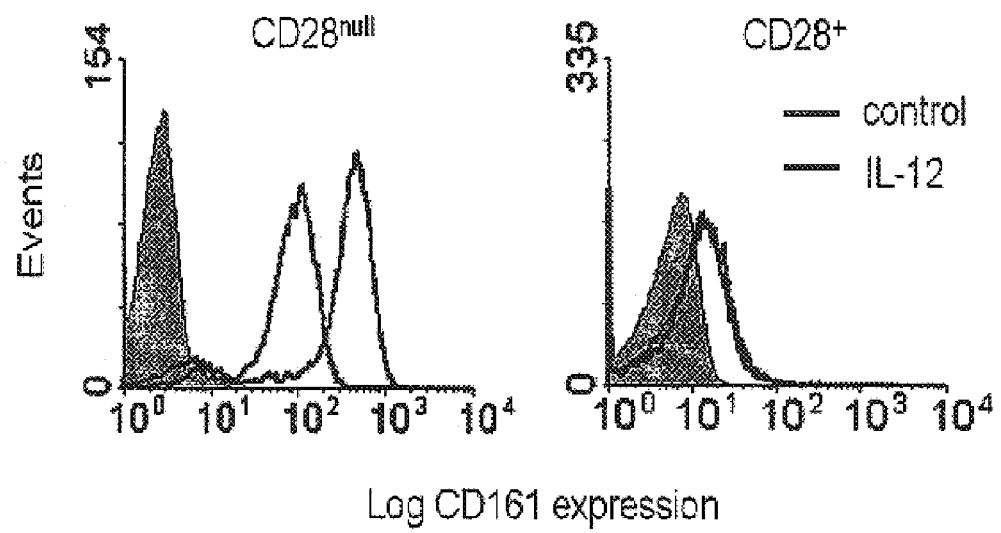
FIG. 12 contains one FACS analysis graph of $CD4^+CD28^{null}$ T cells stained for CD 161 and treated with or without IL-12 and another FACS analysis graph of $CD4^+CD28^+$ T cells stained for CD161 and treated with or without IL-12.

Candidate gene profiling and differential display PCR were used to identify perform and CD161 as molecules that are specifically expressed on CD4+CD28$^{null}$ T cells but not CD4+CD28$^{null}$ T cells. Flow cytometric studies revealed that perform is expressed by all CD4+CD28$^{null}$ T cells whether activated or not. Normal CD4 T cells do not express perforin. In contrast, only a fraction of peripheral CD4+CD28$^{null}$ T cells express CD161, a C-type lectin molecule, in vivo. In addition, CD161 expression was not observed in vitro in resting CD4+CD28$^{null}$ T cells or CD4+CD28+ T cells. Treating CD4+CD28$^{null}$ T cells with IL-12 induced CD161 expression, while treating CD4+CD28+ T cells with IL-12 did not (FIG. 12). These results indicate that CD161 can be used as a marker for activated CD4+CD28$^{null}$ T cells.

To evaluate CD161 expression in vivo, inflamed tissue was obtained from an arthritis patient having a high frequency of peripheral CD4+CD28$^{null}$ T cells. This tissue was stained with anti-CD4 and anti-CD161 antibodies. CD4 was visualized with secondary antibodies and Vector Red alkaline phosphatase. CD161 was visualized with secondary antibodies and horseradish peroxidase. After staining, a substantial fraction of CD4+ T cells was found to express CD161. Staining serial sections confirmed that the cells expressing CD161 also expressed perforin.

Example 13

Identifying Antigens that Activate CD4+CD28$^{null}$ T cells

Comparing TCR β-chain sequences from the different T cell clones identified in samples obtained from UA patients revealed that certain TCR BV-BJ combinations are preferentially used and that the junctional regions of the TCR sequences have a high degree of sequence homology. These findings indicate a common antigen or common set of antigens could be stimulating CD4$^+$CD28$^{null}$ T cells in different UA patients. Such antigens could be microbial antigens indicating that the expansion of CD4$^+$CD28$^{null}$ T cells could result from a chronic persistent infection present in UA patients.

The following procedures are used to isolate antigens that activate CD4$^+$CD28$^{null}$ T cells in UA patients. The HLA-DRB1 alleles in UA patients who have died from myocardial infarction are characterized using PCR-based typing (One Lamda, Canoga Park, Calif.). After characterizing the HLA-DRB1 alleles, antigen presenting cells (e.g., GM-CSF/IL-4 cultured dendritic cells) expressing the appropriate HLA-DRB1 alleles are obtained. Appropriate HLA-DRB 1 alleles are those alleles that are present in the UA patients. Briefly, dendritic cells are obtained from buffy coats of HLA-DRB1-matched donors by T-cell depletion and culturing in IL-4/GM-CSF-containing medium. Once obtained, the antigen presenting cells are transfected with mixtures of clones obtained from differential display PCR or an expression library made using subtractive suppression hybridization. For the subtractive suppression hybridization approach, a selective library is made by obtaining expressed nucleic acid sequences from stable plaques and subtracting that nucleic acid from expressed nucleic acid sequences obtained from unstable plaques using the PCR Select DNA subtraction kit from Clontech. Briefly, poly(A) RNA is extracted from stable and unstable plaques. Double-stranded cDNA is synthesized, blunted with T4 polymerase, and digested with Rsa I (Roche Molecular Biochemicals-Boehringer Mannheim, Indianapolis, Ind.). cDNA derived from the unstable plaque is divided into two equal parts, each of which is ligated to a different adapter (tester cDNA). Subsequently, the tester cDNA is hybridized with the driver PCR from the stable plaque that has not been ligated to an adapter. Unhybridized cDNA is then amplified in a nested PCR approach. Alternatively, expressed nucleic acid sequences from skin fibroblasts are subtracted from expressed nucleic acid sequences obtained from unstable plaques using the PCR Select DNA subtraction kit from Clontech. The expression library can be made using tissue obtained from the same patient from which the expanded CD4$^+$CD28$^{null}$ T cell clones to be tested were obtained.

After transfection, the antigen presenting cells are incubated with CD4$^+$CD28$^{null}$ T-cell clones isolated from UA patients. Briefly, clonally expanded CD4$^+$CD28$^{null}$ T cells are obtained from PBMC samples obtained from UA patients having had fatal myocardial infarction. Once obtained, the CD4$^+$CD28$^{null}$ T cells are activated with immobilized anti-CD3 and cloned by limiting dilution cloning on irradiated EBV blast feeder cells in IL-2-containing medium as described elsewhere (Goronzy et al., *J. Clin. Invest.* 94:2068–76 (1994)). Each expanded CD4$^+$CD28$^{null}$ T cell clone is analyzed to determine its TCR β-chain sequence.

After incubating the antigen presenting cells with the CD4$^+$CD28$^{null}$ T-cell clones, the CD4$^+$CD28$^{null}$ T-cell clones are analyzed to determine whether or not the antigen presenting cells stimulated cytokine secretion. The antigen presenting cells that stimulate a CD4$^+$CD28$^{null}$ T-cell clone are identified as described elsewhere (Brichard et al., *J. Exp. Med.* 178:489–95 (1993)) using IFN-γ ELISA kits as a readout system. Once identified, the antigen presenting cells that stimulate a CD4$^+$CD28$^{null}$ T-cell clone are evaluated to determine the nucleic acid sequence of the antigenic polypeptide.

An algorithm is used to identify immunogenic peptides within the polypeptide identified as stimulating a CD4$^+$CD28$^{null}$ T-cell clone. Candidate peptides are then synthesized and tested in functional assays using the T-cell clones.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining whether or not the cardiovascular system of a mammal has an unstable plaque, said method comprising determining whether or not a sample from said mammal contains an elevated level of a CD64 or IP-10 polypeptide, wherein said elevated level indicates that the cardiovascular system of said mammal contains said unstable plaque.

2. The method of claim 1, wherein said mammal is a human.

3. The method of claim 1, wherein said sample is a blood sample.

4. The method of claim 1, wherein said sample comprises mononuclear cells.

5. A method of assisting a person in determining whether or not the cardiovascular system of a mammal has an unstable plaque, said method comprising:

a) determining the level of a CD64 or IP-10 polypeptide in a sample from the cardiovascular system of said mammal, and b) communicating information about said level to said person, wherein an elevated level of said CD64 or IP-10 polypeptide in said sample indicates that said mammal contains said unstable plaque.

6. The method of claim 5, said person is a medical professional.

7. The method of claim 6, wherein said medical professional is selected from the group consisting of a doctor, a nurse practitioner, a scientist, and a technician.

8. The method of claim 5, wherein said communication comprises sending said information directly to said person.

9. The method of claim 5, wherein said communication comprises sending said information indirectly to said person.

10. The method of claim 5, wherein said communication comprises making said information electronically available to said person.

11. A method for determining whether or not the cardiovascular system of a mammal is at risk for developing an unstable plaque, said method comprising determining whether or not a sample from said mammal contains an elevated level of a CD64 or IP-10 polypeptide, and wherein said elevated level indicates that the cardiovascular system of said mammal is at risk for developing said unstable plaque.

12. A method of assisting a person in determining whether or not the cardiovascular system of a mammal is at risk for developing an unstable plaque, said method comprising:

a) determining the level of a CD64 or IP-10 polypeptide in a sample from said mammal, and b) communicating information about said level to said person, wherein an elevated level of said CD64 or IP-10 polypeptide in said sample indicates that the cardiovascular system of said mammal is at risk for developing said unstable plaque.

* * * * *

UNITED STATES PATENT AND TRADEMARK OFFICE
CERTIFICATE OF CORRECTION

PATENT NO. : 6,962,776 B2  Page 1 of 1
APPLICATION NO. : 09/792686
DATED : November 8, 2005
INVENTOR(S) : Cornelia M. Weyand et al.

It is certified that error appears in the above-identified patent and that said Letters Patent is hereby corrected as shown below:

Title Page, References Cited, Other Publications, Banerjee et al. reference, please delete "MAST" and insert --MALT--therefor;

Title Page, References Cited, Other Publications, Brichard et al. reference, delete please "in" and insert --on--therefor;

Title Page (Page 2), References Cited, Other Publications, DeWood et al. reference, please delete "Prevelance" and insert --Prevalance--therefor;

Title Page (Page 2), References Cited, Other Publications, Fu et al. reference, please delete "Splinic" and insert --Splenic--therefor, Title Page (Page 2), References Cited, Other Publications, Gurfinkel et al. reference, please delete "coronary" and insert --coronary--therefor;

Title Page (Page 3), References Cited, Other Publications, Jander et al. reference, please delete "1652" and insert --1625--therefor;

Title Page (Page 3), References Cited, Other Publications, Lennert and Schmid reference, please delete "Syndroma" and insert --Syndrome--therefor;

Title Page (Page 3), References Cited, Other Publications, first Matsumoto et al. reference, please delete "lymphtoxin" and insert --lymphotoxin--therefor;

Signed and Sealed this

Eighth Day of August, 2006

JON W. DUDAS
*Director of the United States Patent and Trademark Office*

SEQUENCE LISTING

<160> NUMBER OF SEQ ID NOS: 37

<210> SEQ ID NO 1
<211> LENGTH: 18
<212> TYPE: DNA
<213> ORGANISM: Homo sapiens

<400> SEQUENCE: 1
cgccatttcc cgtaaatc                    18

<210> SEQ ID NO 2
<211> LENGTH: 21
<212> TYPE: DNA
<213> ORGANISM: Homo sapiens

<400> SEQUENCE: 2
ggaacctcca gtctcagcac c                21

-continued

```
<210> SEQ ID NO 3
<211> LENGTH: 21
<212> TYPE: DNA
<213> ORGANISM: Homo sapiens

<400> SEQUENCE: 3
cagcctctgt gtggtccatc c                                          21

<210> SEQ ID NO 4
<211> LENGTH: 26
<212> TYPE: DNA
<213> ORGANISM: Homo sapiens

<400> SEQUENCE: 4
atcatgtttg agaccttcaa cacccc                                     26

<210> SEQ ID NO 5
<211> LENGTH: 22
<212> TYPE: DNA
<213> ORGANISM: Homo sapiens

<400> SEQUENCE: 5
caggaggagc aatgatcttg at                                         22

<210> SEQ ID NO 6
<211> LENGTH: 48
<212> TYPE: DNA
<213> ORGANISM: Artificial Sequence
<220> FEATURE:
<223> OTHER INFORMATION: nonspecific oligonucleotide probe

<400> SEQUENCE: 6
tcgaagtact caattgctcg agatcgatag atctgaattc agtactcc             48

<210> SEQ ID NO 7
<211> LENGTH: 21
<212> TYPE: DNA
<213> ORGANISM: Homo sapiens

<400> SEQUENCE: 7
ctgtgcacct ccttcccatt c                                          21

<210> SEQ ID NO 8
<211> LENGTH: 20
<212> TYPE: DNA
<213> ORGANISM: Homo sapiens

<400> SEQUENCE: 8
gtgggagatc tctgcttctg                                            20

<210> SEQ ID NO 9
<211> LENGTH: 18
<212> TYPE: DNA
<213> ORGANISM: Homo sapiens

<400> SEQUENCE: 9
ttctgatggc tcaaacac                                              18

<210> SEQ ID NO 10
<211> LENGTH: 14
<212> TYPE: PRT
<213> ORGANISM: Homo sapiens
```

-continued

```
<400> SEQUENCE: 10

Cys Ala Ser Ser Leu Gly Gly Gly Thr Tyr Glu Gln Phe Phe
 1               5                  10

<210> SEQ ID NO 11
<211> LENGTH: 18
<212> TYPE: DNA
<213> ORGANISM: Homo sapiens

<400> SEQUENCE: 11
ttaggagggg gcacctat                                                  18

<210> SEQ ID NO 12
<211> LENGTH: 14
<212> TYPE: PRT
<213> ORGANISM: Homo sapiens

<400> SEQUENCE: 12

Cys Ala Ser Ser Pro Thr Gly Gly Thr Tyr Glu Gln Phe Phe
 1               5                  10

<210> SEQ ID NO 13
<211> LENGTH: 18
<212> TYPE: DNA
<213> ORGANISM: Homo sapiens

<400> SEQUENCE: 13
cccaccgggg ggacctat                                                  18

<210> SEQ ID NO 14
<211> LENGTH: 14
<212> TYPE: PRT
<213> ORGANISM: Homo sapiens

<400> SEQUENCE: 14

Cys Ala Ser Ser Leu Gly Gly Gly Asp Tyr Asp Gln Tyr Phe
 1               5                  10

<210> SEQ ID NO 15
<211> LENGTH: 18
<212> TYPE: DNA
<213> ORGANISM: Homo sapiens

<400> SEQUENCE: 15
ttaggggggg gcgactat                                                  18

<210> SEQ ID NO 16
<211> LENGTH: 14
<212> TYPE: PRT
<213> ORGANISM: Homo sapiens

<400> SEQUENCE: 16

Cys Ala Ser Ser Ser Gly Gly Gly Thr Tyr Glu Gln Phe Phe
 1               5                  10

<210> SEQ ID NO 17
<211> LENGTH: 18
<212> TYPE: DNA
<213> ORGANISM: Homo sapiens

<400> SEQUENCE: 17
agcggcgggg gcacctat                                                  18
```

```
<210> SEQ ID NO 18
<211> LENGTH: 16
<212> TYPE: PRT
<213> ORGANISM: Homo sapiens

<400> SEQUENCE: 18

Cys Ala Ser Ser Arg Glu Gly Thr Glu Gly Ser Tyr Glu Gln Tyr Phe
 1               5                  10                  15

<210> SEQ ID NO 19
<211> LENGTH: 24
<212> TYPE: DNA
<213> ORGANISM: Homo sapiens

<400> SEQUENCE: 19
cgcgaaggaa cggaagggtc ctat                                           24

<210> SEQ ID NO 20
<211> LENGTH: 15
<212> TYPE: PRT
<213> ORGANISM: Homo sapiens

<400> SEQUENCE: 20

Cys Ala Ser Ser Arg Glu Gly Gly Gly Ser Tyr Glu Gln Tyr Phe
 1               5                  10                  15

<210> SEQ ID NO 21
<211> LENGTH: 21
<212> TYPE: DNA
<213> ORGANISM: Homo sapiens

<400> SEQUENCE: 21
cgcgaagggg ggggtcctat                                                21

<210> SEQ ID NO 22
<211> LENGTH: 14
<212> TYPE: PRT
<213> ORGANISM: Homo sapiens

<400> SEQUENCE: 22

Cys Ala Ser Ser Ser Ser Arg Gly Asp Tyr Glu Gln Tyr Phe
 1               5                  10

<210> SEQ ID NO 23
<211> LENGTH: 18
<212> TYPE: DNA
<213> ORGANISM: Homo sapiens

<400> SEQUENCE: 23
agcagcaggg gcgactat                                                  18

<210> SEQ ID NO 24
<211> LENGTH: 14
<212> TYPE: PRT
<213> ORGANISM: Homo sapiens

<400> SEQUENCE: 24

Cys Ala Ser Ser Ser Ser Arg Gly Thr His Glu Gln Phe Phe
 1               5                  10

<210> SEQ ID NO 25
<211> LENGTH: 18
<212> TYPE: DNA
<213> ORGANISM: Homo sapiens
```

-continued

```
<400> SEQUENCE: 25
agcagtaggg ggacccat                                                   18

<210> SEQ ID NO 26
<211> LENGTH: 13
<212> TYPE: PRT
<213> ORGANISM: Homo sapiens

<400> SEQUENCE: 26

Cys Ala Ser Ser Phe Gly Ala Ser Tyr Glu Gln Tyr Phe
1               5                   10

<210> SEQ ID NO 27
<211> LENGTH: 15
<212> TYPE: DNA
<213> ORGANISM: Homo sapiens

<400> SEQUENCE: 27
ttcggggcct cctat                                                      15

<210> SEQ ID NO 28
<211> LENGTH: 13
<212> TYPE: PRT
<213> ORGANISM: Homo sapiens

<400> SEQUENCE: 28

Cys Ala Ser Ser Tyr Gly Ala Ser Tyr Glu Gln Tyr Phe
1               5                   10

<210> SEQ ID NO 29
<211> LENGTH: 15
<212> TYPE: DNA
<213> ORGANISM: Homo sapiens

<400> SEQUENCE: 29
tacggtgcct cctat                                                      15

<210> SEQ ID NO 30
<211> LENGTH: 7
<212> TYPE: PRT
<213> ORGANISM: Homo sapiens

<400> SEQUENCE: 30

Asp Pro Ala Gly Gly Ala Asp
1               5

<210> SEQ ID NO 31
<211> LENGTH: 7
<212> TYPE: PRT
<213> ORGANISM: Homo sapiens

<400> SEQUENCE: 31

Ser Pro Ala Gly Thr Tyr Asn
1               5

<210> SEQ ID NO 32
<211> LENGTH: 7
<212> TYPE: PRT
<213> ORGANISM: Homo sapiens

<400> SEQUENCE: 32

Ser Leu Gly Thr Thr Gly Asn
1               5
```

```
-continued

<210> SEQ ID NO 33
<211> LENGTH: 6
<212> TYPE: PRT
<213> ORGANISM: Homo sapiens

<400> SEQUENCE: 33

Leu Arg Asp Arg Glu Ser
1               5

<210> SEQ ID NO 34
<211> LENGTH: 5
<212> TYPE: PRT
<213> ORGANISM: Homo sapiens

<400> SEQUENCE: 34

Arg Gln Gly Thr Tyr
1               5

<210> SEQ ID NO 35
<211> LENGTH: 5
<212> TYPE: PRT
<213> ORGANISM: Homo sapiens

<400> SEQUENCE: 35

Pro Thr Ser Glu Asp
1               5

<210> SEQ ID NO 36
<211> LENGTH: 6
<212> TYPE: PRT
<213> ORGANISM: Homo sapiens

<400> SEQUENCE: 36

Ala Ser Ser Tyr Asn Ser
1               5

<210> SEQ ID NO 37
<211> LENGTH: 5
<212> TYPE: PRT
<213> ORGANISM: Homo sapiens

<400> SEQUENCE: 37

Pro Arg Gln Asp Thr
1               5
```